(12) United States Patent
Mor et al.

(10) Patent No.: US 7,790,463 B2
(45) Date of Patent: Sep. 7, 2010

(54) METHODS OF DETERMINING WHETHER A PREGNANT WOMAN IS AT RISK OF DEVELOPING PREECLAMPSIA

(75) Inventors: Gil G. Mor, Cheshire, CT (US); Donna Neale, New Haven, CT (US); Roberto Romero, Grosse Pointe, MI (US)

(73) Assignees: Yale University, New Haven, CT (US); The United States of America as represented by the Department of Health and Human Services, Washington, DC (US)

( * ) Notice: Subject to any disclaimer, the term of this patent is extended or adjusted under 35 U.S.C. 154(b) by 764 days.

(21) Appl. No.: 11/346,694

(22) Filed: Feb. 2, 2006

(65) Prior Publication Data

US 2007/0178605 A1 Aug. 2, 2007

(51) Int. Cl.
  *G01N 33/48* (2006.01)
  *C07K 1/00* (2006.01)
(52) U.S. Cl. ........................................ 436/65; 530/351
(58) Field of Classification Search ........................ None
  See application file for complete search history.

(56) References Cited

U.S. PATENT DOCUMENTS

| 5,108,898 | A * | 4/1992 | Peters et al. ................. 435/7.9 |
| 7,541,182 | B2 | 6/2009 | Mor et al. |
| 2004/0002112 | A1 * | 1/2004 | Mann et al. .................. 435/7.1 |
| 2004/0203037 | A1 * | 10/2004 | Lo et al. ......................... 435/6 |
| 2005/0074746 | A1 | 4/2005 | Mor et al. |

FOREIGN PATENT DOCUMENTS

| WO | WO 02/37120 A2 | 5/2002 |
| WO | WO 2004/088324 A2 | 10/2004 |
| WO | WO 2005/017192 A2 | 2/2005 |
| WO | WO 2007/002967 A3 | 8/2007 |

OTHER PUBLICATIONS

Mellembakken et al., Thromb. Haemost. 86: 1272-1276, 2001.*
Aalkjaer et al. "Morphology and angiotensin II responsiveness of isolated resistance vessels from patients with preeclampsia", *Scand J Clin Lab Invest Suppl* (1984) 169:57-60.
Abrahams et al. "Epithelial Ovarian Cancer secrete funcitonal Fas Ligand", *Cancer Res* 2003;63:5573-5581.
Anonymous. "Do women with preeclampsia, and their babies, benefit from magnesium sulphate? The Magpie Trial: a randomised placebo-controlled trial", *Lancet* (2002) 359:1877-90.
Aschkenazi et al. "Differential regulation and function of the fas/fas ligand system in human trophoblast cells", *Biol Reprod* (2002) 66:1853-61.
Athayde et al. "Interleukin 16 in pregnancy, parturition, rupture of fetal membranes, and microbial invasion of the amniotic cavity", *Am J Obstet Gynecol* (2000) 182:135-41.
Buemi et al. "Is apoptosis cause of preeclampsia?" *Eur Rev Med Pharmacol Sci* (1998) 2:185-8.

Chua et al. "Trophoblast deportation in pre-eclamptic pregnancy", *Br J Obstet Gynaecol* (1991) 98:973-9.
Clark et al. "Plasma endothelin levels in preeclampsia: elevation and correlation with uric acid levels and renal impairment", *Am J Obstet Gynecol* (1992) 166:962-8.
De Wolff et al. "The ultrastructure of acute atherosis in hypertensive pregnancy", *Am J Obstet Gynecol* (1975) 123:164-74.
De Wolff et al."Ultrastructure of the spiral arteries in the human placental bed at the end of normal pregnancy", *Am J Obstet Gynecol* (1973) 117:833-48.
Difederico et al. "Preeclampsia is associated with widespread apoptosis of placental cytotrophoblasts within the uterine wall", *Am J Pathol* (1999) 155:293-301.
Fisher "The placenta dilemma", *Semin Reprod Med* (2000) 18:321-6.
Gant et al. "The nature of pressor responsiveness to angiotensin II in human pregnancy", *Obstet Gynecol* (1974) 43:854.
Gant et al. A Study of Angiotensin II Pressor Response Throughout Primigravid Pregnancy. J. Clin Invest 1973;52:2682-9.
Johansen et al. "Trophoblast deportation in human pregnancy—its relevance for preeclampsia", *Placenta* (1999) 20:531-9.
Kertesz et al. "Purification and characterization of a complex from placental syncytiotrophoblast microvillous membranes which inhibits the proliferation of human umbilical vein endothelial cells", *Placenta* (1999) 20:71-9.
Khong et al. "Inadequate maternal vascular response to placentation in pregnancies complicated by preeclampsia and by small-for-gestational age infants", *Br J Obstet Gynaecol* (1986) 93:1049-59.
Knight et al. "Shedding of syncytiotrophoblast microvilli into the maternal circulation in pre-eclamptic pregnancies", *Br J Obstet Gynaecol* (1998) 105:632-40.
Krege Jh, et al. "A proposed relationship between vasopressinase altered vasopressin and preeclampsia", *Med Hypotheses* (1990) 31:283-7.
Levy et al. "To be, or not to be, that is the question. Apoptosis in human trophoblast", *Placenta* (2000) 21:1-13.
Levy et al. "Trophoblast apoptosis from pregnancies complicated by fetal growth restriction is associated with enhanced p53 expression", *Am J Obstet Gynecol* (2002) 186:1056-61.
McKinney et al. "Plasma, urinary, and salivary 8-epi-prostaglandin f2alpha levels in normotensive and preeclamptic pregnancies", *Am J Obstet Gynecol* (2000) 183:874-7.
Mor et al. "Fas-Fas ligand system induced apoptosis in human placenta and gestational trophoblastic disease", *American Journal of Reproductive Immunology* (1998) 40:89-95.
Mor G et al. "Role of the Fas/Fas ligand system in female reproductive organs: survival and apoptosis.", *Biochem Pharmacol* (2002) 64:1305.

(Continued)

*Primary Examiner*—Robert Landsman
*Assistant Examiner*—Gyan Chandra
(74) *Attorney, Agent, or Firm*—Wolf, Greenfield & Sacks, P.C.

(57) ABSTRACT

The present invention provides methods and compositions related to biomarker profiles for each trimester of pregnancy. The present invention also provides methods for identifying patients at risk of developing a complication of pregnancy, such as preeclampsia. In further embodiments, the present invention relates to methods for the diagnosis of patients with preeclampsia.

22 Claims, 26 Drawing Sheets

OTHER PUBLICATIONS

Nagata "Apoptosis by death factor", *Cell* (1997) 88:355-365.
Neale et al. "Maternal serum of women with preeclampsia reduces trophoblast cell viability: evidence for an increased sensitivity to Fas-mediated apoptosis", *J Matern Fetal Neonatal Med* (2003) 13:39-44.
Pedersen et al. "Renin, angiotensin II, aldosterone, catecholamines, prostaglandins and vasopressin. The importance of pressor and depressor factors for hypertension in pregnancy", *Scand J Clin Lab Invest Suppl* (1984) 169:48-56.
Pirani et al. "The effect of plasma retransfusion on the blood pressure in the puerperium", *Am J Obstet Gynecol* (1975) 121:221-6.
Roberts "Preeclampsia: what we know and what we do not know", *Semin Perinatol* (2000) 24:24-8.
Romero et al. "Further observations on the fetal inflammatory response syndrome: a potential homeostatic role for the soluble receptors of tumor necrosis factor alpha", *Am J Obstet Gynecol* (2000) 183:1070-7.
Rudin et al. "Apoptosis and disease: regulation and clinical relevance of programmed cell death", *Annu Rev Med* (1997) 48:267-81.
Sargent et al. "Clinical experience: isolating trophoblasts from maternal blood", *Ann N Y Acad Sci* (1994) 731:154-61.
Smith et al. "Increased placental apoptosis in intrauterine growth restriction", *Am J Obstet Gynecol* (1997) 177:1395-401.
Smith et al. "Placental apoptosis in normal human pregnancy", *Am J Obstet Gynecol* (1997) 177:57-65.
Song et al. "Hormonal regulation of Fas and FasL expression and apoptosis in the normal human endometrium", *Molecular Human Reproduction* (2002) 8:447-455.
Song et al. "Roles of Fas and Fas ligand during mammary gland remodeling", *J Clin Invest* (2000) 106:1209-20.
Straszewski et al. "Confers Human Trophoblast Cell Resistance to Fas-Mediated Apoptosis", *Molecular Human Reproduction* (2004) 10(1):33-41.
Tatum et al. "The hypertensive action of blood from patients with preeclampsia", Am J Obstet Gynecol 1962;83:1028-35.
Williams "Premature separation of the normally implanted placenta", *Surg Gynecol Obstet* 1915;21:541-554.
Zhou et al. "Preeclampsia is associated with failure of human cytotrophoblasts to mimic a vascular adhesion phenotype. One cause of defective endovascular invasion in this syndrome?", *J Clin Invest* (1997) 99:2152-64.
Zuspan "Catecholamines. Their role in pregnancy and the development of pregnancy-induced hypertension", *J Reprod Med* 1979;23:143-50.
Zuspan "Urinary amine alterations in drug-addiction pregnancy", *Am J Obstet Gynecol* (1976) 126:955-64.
Arriaga-Pizano et al., "The predominant Th1 cytokine profile in maternal plasma of preeclamptic women is not reflected in the choriodecidual and fetal compartments", *J of the Soc for Gynec Invest* (2005) 12:2005-07.
Ashkenazi et al. "Death receptors: signaling and modulation", *Science* (1998) 281:1305-8.
Berridge et al. "Characterization of the cellular reduction of 3-(4,5-dimethylthiazol-2-yl)-2,5-diphenyltetrazolium bromide (MTT): subcellular localization, substrate dependence, and involvement of mitochondrial electron transport in MTT reduction", *Arch Biochem Biophys* (1993) 303:474-82.
Brosens et al. "Fetal growth retardation and the arteries of the placental bed", *Br J Obstet Gynaecol* (1977) 84:656-63.
Chesley et al. "The control of hypertension in pregnancy", *Obstet and Gynec Ann* (1981) 10: 69-106.
Clark et al. "The neutrophil and preeclampsia", *Semin Reprod Endocrinol* (1998) 16:57-64.
Genbacev et al. "Invasive cytotrophoblast apoptosis in preeclampsia", *Hum Reprod* (1999) 14 Suppl 2:59-66.
Gervasi et al. "Phenotypic and metabolic characteristics of maternal monocytes and granulocytes in preterm labor with intact membranes", *Am J Obstet Gynecol* (2001)185:1124-9.
Gonen et al., "Longitudinal assessment of maternal serum placental protein 13 as a predictor of preeclampsia, pregnancy induced hypertension and intrauterine growth restriction", *Amer J of Obstetrics and Genec* (2005) 193:2005-12.
Greer et al. "Neutrophil activation in pregnancy-induced hypertension", *Br J Obstet Gynaecol* (1989) 96:978-82.
Greer et al. "Neutrophil activation is confined to the maternal circulation in pregnancy-induced hypertension", *Obstet Gynecol* (1991) 78:28-32.
Jarvis et al. "Fetal cytokine expression in utero detected by reverse transcriptase polymerase chain reaction", *Pediatr Res* (1995) 37:450-4.
Kim et al. "Failure of physiologic transformation of the spiral arteries in the placental bed in preterm premature rupture of membranes", *Am J Obstet Gynecol* (2002) 187:1137-42.
Loke et al. "Identification of cytotrophoblast colonies in cultures of human placental cells using monoclonal antibodies", *Placenta* (1986) 7:221-31.
Miller et al. "Fetal growth retardation in rats may result from apoptosis: role of peroxynitrite", *Free Radic Biol Med* (1996) 21:619-29.
Nagata "Fas and fas ligand: a death factor and its receptor", *Adv Immunol* (1994) 57:129-135.
Ning et al., "Maternal plasma concentrations of insulinlike growth factor-1 and insulinlike growth factor-binding protein-1 in early pregnancy and subsequent risk of preeclampsia", *Clin Biochem* (2004) 37:2004-11.
Pijnenborg "Establishment of uteroplacental circulation", *Reprod Nutr Dev* (1988) 28:1581-1586.
Polliotti et al. "Second-trimester maternal serum placental growth factor and vascular endothelial growth factor for predicting severe, early-onset preeclampsia", *Obstet Gynecol* (2003) 101:1266-1274.
Rinehart et al. "Expression of the placental cytokines tumor necrosis factor alpha, interleukin 1beta, and interleukin 10 is increased in preeclampsia", *Am J Obstet Gynecol* (1999) 181:915-20.
Roberts et al. "Preeclampsia: more than pregnancy-induced hypertension", *Lancet* (1993) 341:1447-51.
Robertson et al. "Maternal uterine vascular lesions in the hypertensive complications of pregnancy", *Perspect Nephrol Hypertens* (1976) 5:115-27.
Tatum et al. "The obstetric patient with toxemia", *Clin Obstet and Gynecol* (1964) 233-248.
Whitcomb et al., "Evaluation of B-type natriuretric peptide (BNP) levels in patients at elevated risk for preeclampsia". *Amer J of Obstet and Gynecol* (2005) 193:2005-12.
Yoon et al. "Amniotic fluid cytokines (interleukin-6, tumor necrosis factor-alpha, interleukin-1 beta, and interleukin-8) and the risk for the development of bronchopulmonary dysplasia", *Am J Obstet Gynecol* (1997) 177:825-30.
Gynecologists ACoOa. The Compendium. In: ACOG, ed. Hypertension and pregnancy. Washington, DC, 2000. Technical Bulletin, vol. 219.
Hsu et al., Serum soluble Fas levels in preeclampsia. Obstet Gynecol. Apr. 2001;97(4):530-2.

\* cited by examiner

Figure 18.

|  | NORMAL | PRE DISEASE | p value |
|---|---|---|---|
| Number of patients | 58 | 38 | ns |
| Mean age (yrs) | 27.39 | 27.27 | ns |
| Gravida | 2.29 | 1.97 | ns |
| Mean gestational age at blood draw (wks) | 23.14 | 20.38 | ns |
| Nulliparous (N) | 7 | 15 | >.05 |

METHODS OF DETERMINING WHETHER A PREGNANT WOMAN IS AT RISK OF DEVELOPING PREECLAMPSIA

FUNDING

Work described herein was funded, in whole or in part, by National Institutes of Health grant, NICHD, PRB 2NO1 HD23342. The United States government has certain rights in the invention.

BACKGROUND OF THE INVENTION

Preeclampsia is a complication in up to 8% of pregnancies and accounts for significant perinatal morbidity and mortality (1, 2). No definitive etiology or specific predictors of the disease has been identified to date. Furthermore, there has been little progress in the treatment of this disorder; the cure remains delivery of the fetus and removal of the placenta.

As early as 1915, Williams hypothesized the presence of toxic factors in the blood of women with the clinical syndrome of "toxemia" or preeclampsia (25). A number of subsequent studies, aimed at determining whether blood from pregnant women or placental extracts contained factors responsible for hypertension, yielded contradictory results (26-28). Tatum and Mule reported that whole blood collected from patients with severe preeclampsia could induce transient hypertension when transfused to the same patient in the post partum period (28). Pirani and Macgillivray reported similar observations after injecting plasma from eclamptic women 6 days after delivery (29). Since the increase in blood pressure could not be elicited by re-transfusion 6 weeks postpartum, the authors concluded that patients with preeclampsia had increased sensitivity to pressor agent(s) lasting about 1 week after delivery, but not as long as 6 weeks. Thereafter, considerable effort was devoted to the identification of the pressor agent responsible for this effect in the maternal circulation. Over the years, the focus has encompassed the renin-angiotensin system (30, 31), norepinephrine (32, 33), vasopressin (34), prostaglandins (35), endothelin (36) and others (37, 38). Despite all efforts, the factor(s) responsible for these effects remains to be elucidated.

The hallmark of normal placentation is the invasion of trophoblast cells into the decidual and myometrial segments of the spiral arteries, resulting in the reversible obliteration of the normal arterial wall architecture (3). Muscular, medial elastic, and endothelial layers of the arteriolar walls are invaded by trophoblasts and replaced by fibrinoid material, converting narrow-lumen spiral arteries into large-bore uteroplacental vessels (4). In contrast, failure of physiologic transformation of the myometrial segment of the spiral arteries is characteristic of abnormal placentation and has been considered central to the pathophysiology of preeclampsia for the past 30 years (5, 3, 6). Moreover, recent microscopic studies of placental specimens from women with preeclampsia have demonstrated that the extra villous trophoblasts anchoring the placenta to the uterine wall show marked apoptosis as early as the first trimester (7, 8), suggesting that the initial insult occurs early in gestation and may involve the trophoblast (9, 10, 11).

Around the second postconceptional week, the cytotrophoblast and syncytiotrophoblast differentiate from the implanted blastocyst (47). The cytotrophoblast divides to form syncytiotrophoblasts and further proliferates to form a specialized trophoblast referred to as an extravillous trophoblast. It is the extravillous trophoblast that extends through the endometrium to reach the border of the decidua and myometrium. The extravillous trophoblast continues its invasion into the spiral arterioles and replaces the endothelial and muscular linings of the uterine arterioles, leading to vasodilation of the uterine vasculature (7). This change ensures a continued low resistance system, which potentiates maternal blood flow to the intervillous space and maintains adequate perfusion of the developing fetus.

In preeclampsia, with the absence of marked vasodilation and with the lumen of the vessels essentially occluded, blood flow and oxygen transfer to the fetus is diminished, leading to the maternal manifestations of preeclampsia as well as the fetal manifestations of oligohydramnios and intrauterine growth restriction (IUGR). One theory to explain the etiology of preeclampsia implicates an injured placenta leading to hypoperfusion of the implantation site and endothelial cell damage (48).

It would be useful to be able to identify patients at risk of developing preeclampsia.

SUMMARY OF THE INVENTION

The present invention relates to methods for determining or aiding in the determination that a pregnant woman is at risk of developing preeclampsia. In certain embodiments, the invention relates to methods for determining or aiding in the determination that a pregnant woman has preeclampsia.

Applicants hypothesized that the factors regulating trophoblast survival are present in maternal serum, may be detected early in pregnancy and can be evaluated in vitro. Applicants demonstrate that serum from women destined to develop preeclampsia significantly reduced trophoblast cell viability. Furthermore, this effect on cell viability is apparent as early as the first trimester. In addition, this effect is related to the activation of the apoptotic cascade in trophoblast cells. This finding is consistent with the hypothesis that the initiating cellular events leading to preeclampsia occur early in pregnancy and certainly before the development of clinical signs of the disease.

Given that appropriate placentation should occur by the end of the first trimester, it may be possible to detect evidence of aberrant placentation, which may lead to adverse pregnancy outcomes such as preeclampsia, as early as the second trimester.

In certain embodiments, the invention provides a method for determining or aiding in the determination that a pregnant woman is at risk of developing preeclampsia, comprising comparing the expression of one or more biomarkers in a blood sample from the pregnant woman to be assessed for risk of developing preeclampsia to a predetermined standard for each of said one or more biomarkers, wherein a significant difference in expression of the one or more biomarkers in the sample as compared to a predetermined standard of each of the one or more biomarkers indicates that the pregnant woman is at risk of developing preeclampsia, thereby determining or aiding in the determination that the pregnant woman is at risk of developing preeclampsia. Examples of suitable biomarkers include IFNg, I-309, GM-CSF, GDNF, GCP-2, Fraktalkine, Flt-3 Ligand, FGF-7, FGF-6, Eotaxin-3, Eotaxin-2, Eotaxin, EGF, CNTF, CK b 8-1, BMP-6, BMP-4, BLC, BDNF, ANG, MCP-1, LIGHT, Leptin, IL-7, IL-6, IL-5, IL-4, IL-3, IL-2, IL-1ra, IL-1b, IL-1a, IL-16, IL-15, IL-13, IL-10, IGF-1, IGFBP-4, IGFBP-2, IGFBP-1, TNFB, TNFA, TGF-B3, TGF-B1, TARC, SDF-1, SCF, RANTES, PDGF-BB, PARC,NT-3, NAP-2, MIP-3A, MIP-1D, MIG, MDC, M-CSF, MCP-4, MCP-3, MCP-2, Lymphotactin, I-TAC, IL-8, IL-6R, IL-1Ra, IL-17, IL-12 P70, IL-12 P40, IL-11, IL-1R1, IL-1 R4/ST2, IGF-1SR, IGFBP-6, IGFBP-3, ICAM- 3, ICAM-1, HGF, HCC-4, GRO-A, GRO, VEGF-D, VEGF, uPAR, TRAIL R4, TRAIL R3, Thrombopoietin, TIMP-2, TIMP-1, TECK, sTNF RI, sTNF RII, SGP130, PIGF, Oncostatin M, Steoprotegin, NT-4, MSP-A, MIP-3B, MIP-1B, MIP-1A, MIF, Fas, FasL, and tissue factor. In certain embodiments, the one or more biomarkers are selected from the group consisting of: Ang, Leptin, RANTES, PDGF, ICAM 1, VEGF, G-CSF, Fas, EGF, IGFBP 1, MCP 1, IL8, and FasL. In some embodiments, the predetermined standard corresponds to the expression levels of the one or more biomarkers in a pregnant woman who is not at risk of developing preeclampsia. In certain embodiments, in which the pregnant woman to be assessed for risk of developing preeclampsia is in the first trimester of pregnancy, the predetermined standard corresponds to the expression levels of the one or more biomarkers in the first trimester of pregnancy. In other embodiments, in which the pregnant woman to be assessed for risk of developing preeclampsia is in the second trimester of pregnancy, the predetermined standard corresponds to the expression levels of the one or more biomarkers in the second trimester of pregnancy. In yet other embodiments, in which the pregnant woman to be assessed for risk of developing preeclampsia is in the third trimester of pregnancy, the predetermined standard corresponds to the expression levels of said one or more biomarkers in the third trimester of pregnancy.

In certain embodiments, the blood sample is a whole blood sample. In other embodiments, the blood sample is serum.

In certain embodiments, in which the determination of risk of developing preeclampsia is based on a score-based classification method, the method comprises comparing the expression of two or more biomarkers.

In other embodiments, the method of determining or aiding in the determination that a pregnant woman is at risk of developing preeclampsia comprises comparing the expression of two or more biomarkers. In these embodiments, the determination of risk of developing preeclampsia is made by comparing the expression profile of the two or more biomarkers to a predetermined standard profile for the biomarkers; a difference in the profiles determines or aids in the determination that a pregnant woman is at risk of developing preeclampsia. For example, the two or more biomarkers in the pregnant woman being assessed for risk of developing preeclampsia may each be higher or may each be lower than the levels of the corresponding biomarkers in the predetermined standard, thereby determining or aiding in the determination that the pregnant who is at risk of developing preeclampsia. In other embodiments, at least one biomarker may be higher and another biomarker may be lower than the predetermined standard.

In certain embodiments, the predetermined standard profile corresponds to the expression profile of the two or more biomarkers in a pregnant woman who is not at risk of developing preeclampsia. In certain embodiments, in which the pregnant woman to be assessed for risk of developing preeclampsia is in the first trimester of pregnancy, the predetermined standard profile corresponds to the expression profile of the two or more biomarkers in the first trimester of pregnancy. In other embodiments, in which the pregnant woman to be assessed for risk of developing preeclampsia is in the second trimester of pregnancy, the predetermined standard profile corresponds to the expression profile of said two or more biomarkers in the second trimester of pregnancy. In yet other embodiments, in which the pregnant woman to be assessed for risk of developing preeclampsia is in the third trimester of pregnancy, the predetermined standard profile corresponds to the expression profile of the two or more biomarkers in the third trimester of pregnancy. In certain embodiments, the predetermined standard profile is determined by comparing the expression of the two or more biomarkers in a pregnant woman to be assessed for risk of developing preeclampsia to the levels of expression of the two or more biomarkers in a pregnant woman who is not at risk of developing preeclampsia by using a machine learning technique. In some embodiments, the predetermined standard profile is determined by comparing the expression of the two or more biomarkers in the pregnant woman to be assessed for risk of developing preeclampsia to the levels of expression of the two or more biomarkers in a pregnant woman who is not at risk of developing preeclampsia by using support vector machines, K-nearest neighbor classifier, or classification tree analysis.

In certain embodiments, the one or more biomarkers is selected from the group consisting of: Ang, Leptin, RANTES, PDGF, ICAM 1, VEGF, G-CSF, and Fas, and an increase in the expression of the biomarker, compared to the predetermined standard, indicates that the pregnant woman is at risk of developing preeclampsia.

In other embodiments, the one or more biomarkers is selected from the group consisting of: EGF, IGFBP 1, MCP 1, IL8, and FasL, and a decrease in the expression of the biomarker, compared to the predetermined standard, indicates that the pregnant woman is at risk of developing preeclampsia.

The expression of the one or more biomarkers can be detected using a reagent that detects the one or more biomarkers. In some embodiments, the reagent is an antibody or fragment thereof that binds the biomarker. In further embodiments, the reagent is directly or indirectly labeled with a detectable substance. In certain embodiments, the expression of the one or more biomarkers is detected using mass spectroscopy.

In certain embodiments, the expression of the one or more biomarkers is detected by: (a) detecting the expression of a polypeptide which is regulated by the one or more biomarker; (b) detecting the expression of a polypeptide which regulates the biomarker; or (c) detecting the expression of a metabolite of the biomarker.

In other embodiments, the invention relates to a kit for determining if a pregnant woman is at risk of developing preeclampsia. The kit comprises: a receptacle for receiving a sample; one or more reagents for detecting one or more biomarkers selected from the group consisting of: Ang, Leptin, RANTES, PDGF, ICAM 1, VEGF, G-CSF, Fas, EGF, IGFBP 1, MCP 1, IL8, and FasL; a reference sample; and instructions for use. In certain embodiments, the kit comprises one or more reagents for detecting two or more biomarkers.

In some embodiments, the invention relates to a kit comprising one or more reagents for detecting two or more biomarkers selected from the group consisting of: IFNg, I-309, GM-CSF, GDNF, GCP-2, Fraktalkine, Flt-3 Ligand, FGF-7, FGF-6, Eotaxin-3, Eotaxin-2, Eotaxin, EGF, CNTF, CK b 8-1, BMP-6, BMP-4, BLC, BDNF, ANG, MCP-1, LIGHT, Leptin, IL-7, IL-6, IL-5, IL-4, IL-3, IL-2, IL-1ra, IL-1b, IL-1a, IL-16, IL-15, IL-13, IL-10, IGF-1, IGFBP-4, IGFBP-2, IGFBP-1, TNFB, TNFA, TGF-B3, TGF-B1, TARC, SDF-1, SCF, RANTES, PDGF-BB, PARC, NT-3, NAP-2, MIP-3A, MIP-1D, MIG, MDC, M-CSF, MCP-4, MCP-3, MCP-2, Lymphotactin, I-TAC, IL-8, IL-6R, IL-1 Ra, IL-17, IL-12 P70, IL-12 P40, IL-11, IL-1R1, IL-1 R4/ST2, IGF-1SR, IGFBP-6, IGFBP-3, ICAM-3, ICAM-1, HGF, HCC-4, GRO-A, GRO, VEGF-D, VEGF, uPAR, TRAIL R4, TRAIL R3, Thrombopoietin, TIMP-2, TIMP-1, TECK, sTNF RI, sTNF RII, SGP130, PIGF, Oncostatin M, Steoprotegin, NT-4, MSP-A, MIP-3B, MIP-1B, MIP-1A, MIF, Fas, FasL, and tissue factor. In certain embodiments, the biomarkers are selected from the group consisting of: Ang, Leptin, RANTES, PDGF, ICAM 1, VEGF, G-CSF, Fas, EGF, IGFBP 1, MCP 1, IL8, and FasL. In some embodiments, the kit further comprises a reference sample.

In some embodiments, the biomarkers correspond to a protein profile specific for the first, second, and/or third trimester of pregnancy. In certain embodiments, the biomarkers correspond to a protein profile specific for the first trimester of pregnancy. In other embodiments, the biomarkers correspond to a protein profile specific for the second trimester of pregnancy. In yet other embodiments, the biomarkers correspond to a protein profile specific for the third trimester of pregnancy. In certain embodiments, the biomarkers corresponding to a protein profile specific for the first trimester of pregnancy are at least three biomarkers selected from the group consisting of: ANG, Leptin, RANTES, PDGF, ICAM 1, VEGF, G-CSF, Fas, EGF, IGFBP 1, MCP 1, IL8, and FasL.

In other embodiments, the invention relates to a method to screen for a candidate compound useful to treat preeclampsia, comprising: (a) identifying a candidate compound which regulates the expression of one or more biomarkers selected from the group consisting of: Ang, Leptin, RANTES, PDGF, ICAM 1, VEGF, G-CSF, Fas, EGF, IGFBP 1, MCP 1, IL8, and FasL; and (b) determining whether such candidate compound is effective to treat preeclampsia. In further embodiments, the method comprises identifying a candidate compound or a combination of compounds that regulates the expression of two or more biomarkers.

In certain embodiments, the invention relates to a method of screening for candidate preeclampsia risk biomarkers, comprising: (a) identifying two or more biomarkers that are potentially associated with a risk of developing preeclampsia; (b) comparing the level of expression of the biomarkers identified in (a) in a first population of pregnant women at risk of developing preeclampsia to the expression of the two or more biomarkers in pregnant women not at risk of developing preeclampsia; (c) selecting biomarkers exhibiting a significant difference in expression in the first population of pregnant women at risk of developing preeclampsia; (d) comparing the level of expression of the biomarkers identified in (c) in a second population of pregnant women at risk of developing preeclampsia to the expression of the two or more biomarkers in pregnant women not at risk of developing preeclampsia; and (e) selecting biomarkers exhibiting a significant difference in expression in the second population of pregnant women at risk of developing preeclampsia, wherein the biomarkers identified in (e) are candidate preeclampsia risk biomarkers. In certain embodiments, the method further comprises (f) comparing the level of expression of the biomarkers identified in (e) in a third population of pregnant women at risk of developing preeclampsia to the expression of the two or more biomarkers in pregnant women not at risk of developing preeclampsia, wherein the expression of the biomarkers is detected by using a different assay format; and (g) selecting biomarkers exhibiting a significant different in expression in said third population of pregnant women at risk of developing preeclampsia, wherein the biomarkers identified in (g) are candidate biomarkers for risk of developing preeclampsia. In some embodiments, the method further comprises determining whether, in a blind study, the biomarkers identified in (e) distinguish between a pregnant woman at risk of developing preeclampsia and a pregnant woman not at risk of developing preeclampsia. In yet other embodiments, the method further comprises determining whether, in a blind study, the biomarkers identified in (g) distinguish between a pregnant woman at risk of developing preeclampsia and a pregnant woman not at risk of developing preeclampsia.

In certain embodiments, the invention provides a method for determining or aiding in the determination that a pregnant woman is at risk of developing preeclampsia, comprising comparing the expression of one or more biomarkers in a blood sample from the pregnant woman to be assessed for risk of developing preeclampsia to a predetermined standard for each of the one or more biomarkers, wherein a significant difference in expression of the one or more biomarkers in the sample as compared to a predetermined standard of each of the one or more biomarkers indicates that the pregnant woman is at risk of developing preeclampsia, thereby determining or aiding in the determination that the pregnant woman is at risk of developing preeclampsia. In some embodiments, the method further comprises (a) culturing human trophoblast cells in the presence of serum or plasma obtained from the pregnant woman to be assessed for risk of developing preeclampsia; (b) culturing an equivalent sample of human trophoblast cells under the same conditions as cells in (a) but in the absence of serum or plasma obtained from the pregnant woman to be assessed for risk of developing preeclampsia; and (c) comparing viability of cells cultured in (a) with the viability of cells cultured in (b), wherein if fewer cells cultured in (a) than cells cultured in (b) are viable, the pregnant woman is determined to be at risk of developing preeclampsia. In certain embodiments, the method further comprises (d) determining if cells cultured in (a) undergo apoptosis and (e) determining if cells cultured in (b) undergo apoptosis, wherein if more cells cultured in (a) undergo apoptosis than cells cultured in (b), the pregnant woman is determined to be at risk of developing preeclampsia. In yet other embodiments, the method further comprises: (d)culturing an equivalent sample of human trophoblast cells under the same conditions as cells in (a) but in the presence of serum or plasma obtained from a normal control; and (e) comparing viability of cells cultured in (a) with the viability of cells cultured in (d), wherein if fewer cells cultured in (a) than cells cultured in (d) are viable, the pregnant woman is at risk of developing preeclampsia.

In certain embodiments, the invention provides a method for determining or aiding in the determination that a pregnant woman is at risk of developing preeclampsia, comprising comparing the expression of one or more biomarkers in a blood sample from the pregnant woman to be assessed for risk of developing preeclampsia to a predetermined standard for each of the one or more biomarkers, wherein a significant difference in expression of the one or more biomarkers in the sample as compared to a predetermined standard of each of the one or more biomarkers indicates that the pregnant woman is at risk of developing preeclampsia, thereby determining or aiding in the determination that the pregnant woman is at risk of developing preeclampsia. In other embodiments, the method further comprises (a) culturing human trophoblast cells in the presence of (i) anti-Fas antibodies and (ii) serum or plasma obtained from the pregnant woman to be assessed for risk of developing preeclampsia; (b) culturing an equivalent sample of human trophoblast cells under the same conditions as cells in (a) but in the absence of serum or plasma obtained from the pregnant woman to be assessed for risk of developing preeclampsia; and (c) comparing viability of cells cultured in (a) with the viability of cells cultured in (b), wherein if fewer cells cultured in (a) than cells cultured in (b) are viable, the pregnant woman is determined to be at risk of developing preeclampsia.

In yet other embodiments, the invention provides a method for determining or aiding in the determination that a pregnant woman is at risk of developing preeclampsia, comprising comparing the expression of one or more biomarkers in a blood sample from the pregnant woman to be assessed for risk of developing preeclampsia to a predetermined standard for each of the one or more biomarkers, wherein a significant difference in expression of the one or more biomarkers in the sample as compared to a predetermined standard of each of the one or more biomarkers indicates that the pregnant woman is at risk of developing preeclampsia, thereby determining or aiding in the determination that the pregnant woman is at risk of developing preeclampsia. In certain embodiments, the method further comprises (a) culturing human trophoblast cells in the presence of anti-Fas antibodies; (b) culturing cells from (a) in the presence of serum or plasma obtained from the pregnant woman to be assessed for risk of developing preeclampsia; (c) culturing an equivalent sample of cells from (a) under the same conditions as cells in (b) but in the absence of serum or plasma obtained from the pregnant woman to be assessed for risk of developing preeclampsia; and (d) comparing viability of cells cultured in (b) with the viability of cells cultured in (c), wherein if fewer cells cultured in (b) than cells cultured in (c) are viable, the pregnant woman is determined to be at risk of developing preeclampsia. In other embodiments, the method further comprises: (d) culturing an equivalent sample of human trophoblast cells under the same conditions as cells in (a) but in the presence of serum or plasma obtained from a normal control; and (e) comparing viability of cells cultured in (a) with the viability of cells cultured in (d), wherein if fewer cells cultured in (a) than cells cultured in (d) are viable, the pregnant woman is at risk of developing preeclampsia.

In certain embodiments, the invention provides a method for determining or aiding in the determination that a pregnant woman is at risk of developing preeclampsia, comprising comparing the expression of one or more biomarkers in a blood sample from the pregnant woman to be assessed for risk of developing preeclampsia to a predetermined standard for each of the one or more biomarkers, wherein a significant difference in expression of the one or more biomarkers in the sample as compared to a predetermined standard of each of the one or more biomarkers indicates that the pregnant woman is at risk of developing preeclampsia, thereby determining or aiding in the determination that the pregnant woman is at risk of developing preeclampsia. In other embodiments, the method further comprises (a) culturing human trophoblast cells in the presence of serum or plasma obtained from the pregnant woman to be assessed for risk of developing preeclampsia; (b) culturing a sample of human trophoblast cells equivalent to cells cultured in (a) under the same conditions as cells in (a), but in the absence of serum or plasma obtained from the pregnant woman to be assessed for risk of developing preeclampsia; (c) determining if cells cultured in (a) undergo apoptosis; (d) determining if cells cultured in (b) undergo apoptosis, wherein if more cells cultured in (a) undergo apoptosis than cells cultured in (b), the pregnant woman is determined to be at risk of developing preeclampsia. In certain embodiments, the method further comprises (e) culturing a sample of cells equivalent to those cultured in (a), but in the presence of serum or plasma obtained from a normal control; and (f) determining if cells cultured in (e) undergo apoptosis, wherein if more cells cultured in (a) undergo apoptosis than cells cultured in (e) the pregnant woman is determined to be at risk of developing preeclampsia. Apoptosis in (c) and (d) can be determined by detecting an apoptotic marker. In some embodiments, the apoptotic marker is active caspase-3. In further embodiments, the active caspase-3 is selected from p17 and p19. In yet other embodiments, the method further comprises: (d) culturing a sample of cells equivalent to cells cultured in (a) under the same conditions as cells in (b), but in the presence of serum or plasma obtained from a normal control; and (f) comparing viability of cells cultured in (b) with the viability of cells cultured in (e), wherein if fewer cells cultured in (b) than cells cultured in (e) are viable, the pregnant woman is at risk of developing preeclampsia.

In other embodiments, the invention relates to a kit for determining if a pregnant woman is at risk of developing preeclampsia, comprising: (a) a receptacle for receiving a sample; (b) one or more reagents for detecting one or more biomarkers selected from the group consisting of: Ang, Leptin, RANTES, PDGF, ICAM 1, VEGF, G-CSF, Fas, EGF, IGFBP 1, MCP 1, IL8, and FasL; (c) a reference sample; (d) trophoblast cells; (e) media suitable for growth of trophoblast cells; (f) a container for culturing trophoblast cells; and (g) instructions for use. In some embodiments, the trophoblast cells are H8 trophoblast cells. In certain embodiments, the kit contains one or more reagents in (b) for detecting at least three biomarkers selected from the group consisting of: Ang, Leptin, RANTES, PDGF, ICAM 1, VEGF, G-CSF, Fas, EGF, IGFBP 1, MCP 1, IL8, and FasL.

BRIEF DESCRIPTION OF THE DRAWINGS

FIGS. 15A-15C are bar graphs depicting the serum levels as assessed by Luminex® assays of the indicated proteins in the first trimester of normal and prediseased pregnancies.

FIG. 18 is a table depicting the patient characteristics relating to the data presented in FIGS. 18-20.

DETAILED DESCRIPTION OF THE INVENTION

I. Overview

Figure 1:
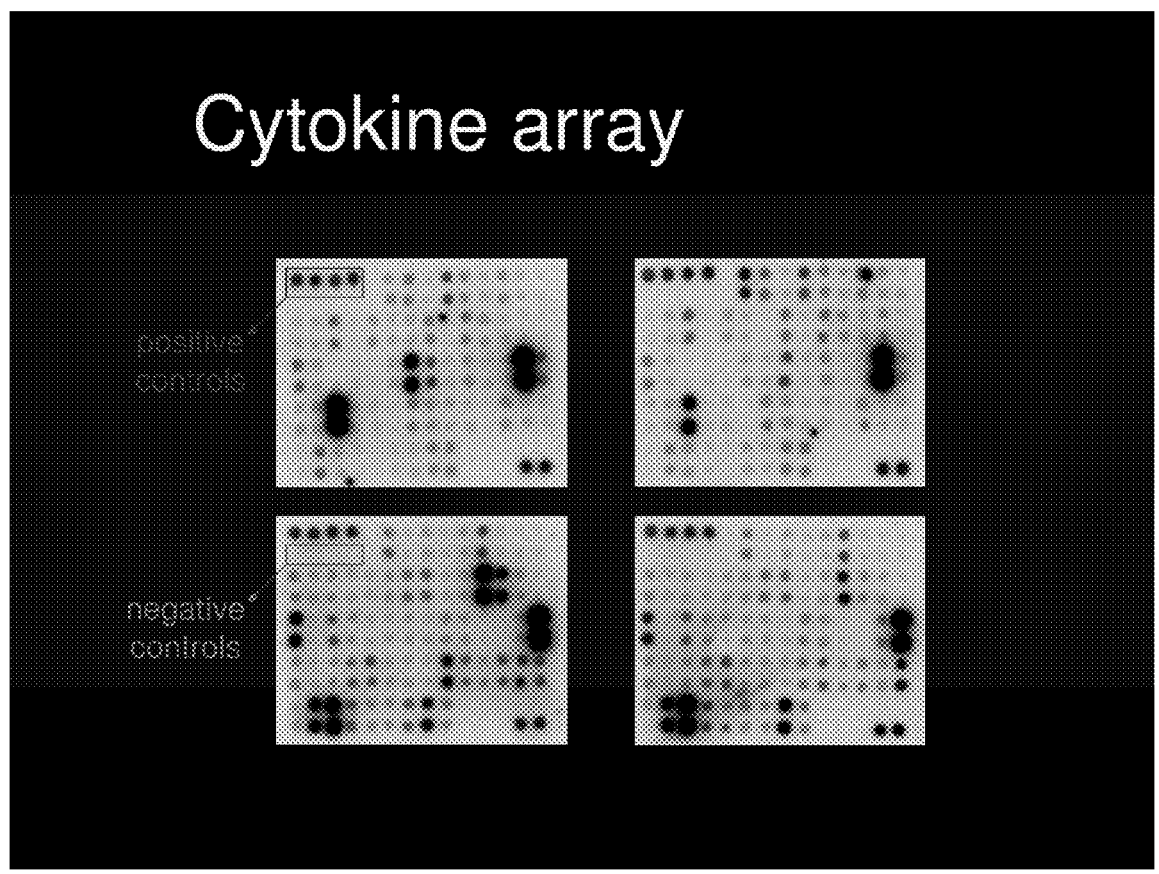
FIG. 1 depicts a cytokine array.

Described herein are methods and compositions related to the detection and/or monitoring the progression of pregnancy in the first, second, and/or third trimester, as well as complications of pregnancy, such as preeclampsia. The "progression of pregnancy" refers to the various stages or phases of pregnancy, including pregnancy throughout each trimester and during the transition from one trimester to the next. The "progression of pregnancy" includes the course of pregnancy in both normal pregnancies and pregnancies in which a complication develops. In some embodiments, the methods and compositions described herein are useful to detect and/or aid in the detection of pregnancy complications or risk of developing pregnancy complications such as intrauterine growth restriction (IUGR), preterm labor, and/or recurrent spontaneous abortion.

The methods and compositions described herein enable one to assess and/or monitor the progression of pregnancy in a female by detecting and/or monitoring the levels of biomarkers that are specific to one or more trimesters in the pregnant female. As used herein, the term "biomarker" refers to one or more molecules, such as polypeptides or nucleic acids (e.g., DNA, RNA) that can be used to: detect, or aid in the detection of, pregnancy and/or pregnancy complications, either alone or as a combination of multiple polypeptides and/or nucleic acids; detect, or aid in the detection of, risk of developing a pregnancy complication; monitor the progression of pregnancy and/or a pregnancy complication; and/or monitor the effectiveness of a treatment for a pregnancy complication. Examples of suitable biomarkers include cytokines, chemokines, growth factors, and apoptotic factors. As used herein, the term "polypeptide" refers to a polymer of amino acids, and not to a specific length. Thus, peptides, oligopeptides and proteins are included within the definition of polypeptide. For convenience, the term "determining" or "determination" is often used herein. It is intended that determining includes aiding in determining and determination includes aiding in the determination. Similarly, it is intended that "diagnose" includes aiding in the diagnosis of and "assess" includes assisting in the assessment of.

Applicants describe a novel method and related compositions by which to assess pregnancy and/or to detect the risk of developing a complication of pregnancy, such as preeclampsia. Described herein are methods and compositions related to the detection of one or more biomarkers, the expression levels of which are correlated to the first, second, and/or third trimester of pregnancy. Previously, the three trimesters of pregnancy in the human female were viewed as one entity. Applicants herein describe methods and related compositions enabling the skilled artisan to assess each trimester of pregnancy as a separate biological condition in the pregnant female.

Applicants demonstrate that the first trimester of pregnancy (weeks 1-12) is characterized by an inflammatory environment. Without wishing to be bound by theory, Applicants hypothesize that this is due to embryo implantation, which results in tissue damage, trophoblast invasion, and maternal immune cell migration. The process of trophoblast invasion of the endometrium and neovascularization requires an inflammatory process. During weeks 12-18, under normal conditions of pregnancy, there is a shift to an anti-inflammatory environment, which characterizes the second trimester (weeks 13-27). Without wishing to be bound by theory, Applicants hypothesize that this occurs in order to promote growth of the developing embryo. During the third trimester (weeks 28-40), Applicants demonstrate that the biological environment shifts back to an inflammatory environment. Without wishing to be bound by theory, Applicants hypothesize that this serves to induce normal parturition.

Applicants have shown that a biomarker profile that is specific to each trimester of pregnancy can be established in a pregnant woman. A standard biomarker profile can be used for comparison to the biomarker profile of a pregnant woman to be assessed for risk of developing a complication of pregnancy, such as preeclampsia. For example, by comparing the level(s) of one or more biomarkers in the serum of a pregnant woman to be assessed for risk of developing preeclampsia to the level(s) of the corresponding one or more biomarkers in the biomarker standard profile, one can determine if there are differences between the two biomarker profiles. The biomarker standard profile may be preestablished or established by assessing serum run concurrently biomarker levels in a normal control (e.g., serum from a pregnant woman who does not develop a pregnancy complication, such as preeclampsia).

In some embodiments, the differences between the two biomarker profiles are significant differences. As used herein, the term "significant difference" is well within the knowledge of a skilled artisan and can be determined empirically with reference to each particular biomarker or panel of biomarkers. For example, a significant difference in the serum level of a biomarker in a subject at risk of developing preeclampsia as compared to a healthy subject (one not at risk of developing preeclampsia) is any difference in serum level that is statistically significant (for example, level=$p<0.05$).

Statistical cluster analysis can be performed on protein biomarkers obtained from patient serum in order to differentiate between normal pregnancies and pregnancies at risk of developing a complication, such as preeclampsia. Three commonly used classification methods can be used: support vector machine (SVM), k-nearest neighbors (kNN), and classification trees (Hastie, et al. (2001) *The Elements of Statistical Learning*, Springer, N.Y.). 10-fold cross validation can be used to evaluate the classification accuracy.

In addition to these three classification methods, a score-based classification method that may be more biologically interpretable can be used. The score-based classification system can be carried out as follows: (i) For each marker, find the best split point to minimize the number of misclassified subjects. The split point defines two intervals: one for normal pregnancy and another for pregnancy destined to be complicated by preeclampsia. A score of 0 is assigned to a subject if its related observation falls in the normal interval; otherwise, a score of 1 is assigned. (ii) Overall, a subject is assigned a score as the sum of these assigned scores from m different markers. Therefore, the range of such score is between 0 and m. (iii) A given threshold (t) is used to predict the disease status for a given subject, e.g., a given woman with a total score equal or less than t is predicted to have normal status (e.g., pregnancy not destined to be complicated by preeclampsia), whereas a subject with a score higher than t will be diagnosed to have disease or likely to develop a disease (e.g., pregnancy destined to be complicated by preeclampsia).

The "split point" described above in connection to the described score based classification system may be identified as follows: Suppose there are n samples classified into two groups. For each marker X, let x-1, x-2, . . . , x-n be the observed measurements. Screen (n−1) split points y-1, y-2, . . . , y-(n−1), where y-k=0.5*(x-k+x-(k+1) ) for k=1, 2, . . . , n−1. For each split point y-k, there are a-1 and a-2 observed measurements less than y-k in the first and the second groups, respectively; and there are b-1 and b-2 observed measurements greater than y-k in the first and the second groups, respectively. If the left and the right sides of y-k are assigned to the first and the second groups, respectively, then there are a-2 and b-1 misclassified samples. If the left and the right sides of y-k are assigned to the second and the first groups, respectively, then there are a-1 and b-2 misclassified samples. Choose the assignment that minimizes the number of misclassified samples.

In certain embodiments of the invention, a predetermined standard for a biomarker profile is established that is specific to each trimester of pregnancy in a healthy subject. As used herein, a "predetermined standard" for a biomarker refers to the level of expression of the biomarker in healthy subjects. The predetermined standard expression levels for a given biomarker can be established by prospective and/or retrospective statistical studies using only routine experimentation. The predetermined standard expression levels can be determined by a person having ordinary skill in the art using well known methods.

The term "healthy subject" and "normal control" are used interchangeably and refer to a pregnant female who does not have and is not at risk of developing a complication of pregnancy, including preeclampsia, IUGR, pre-term labor, and/or spontaneous abortion. Thus, for example, in a method to detect a patient's risk of developing preeclampsia, a "healthy subject" refers to a pregnant female who does not have preeclampsia and is not at risk of developing preeclampsia. Similarly, a "normal pregnancy" refers to a pregnancy that is not complicated by and does not develop a complication of pregnancy.

The predetermined standards provided by certain embodiments of the instant invention enable the skilled artisan to compare the levels of one or more biomarkers in a pregnant woman to be assessed for developing a complication of pregnancy, such as preeclampsia, to the predetermined standard. As such, the methods and compositions of the present invention are useful for the detection or to aid in the detection of abnormalities in the inflammatory or anti-inflammatory processes that occur during one or more trimesters in the pregnant woman. For example, increased levels of inflammatory cytokines in the first trimester may be detected by comparison to a predetermined standard of inflammatory cytokine levels for the first trimester. These results may then be used to assess, for example, whether a woman is at an increased risk of rejecting the developing embryo. In other embodiments, detection of reduced levels of inflammatory cytokines in the first trimester may be useful to diagnose, for example, whether a woman is at increased risk of abnormal placental development.

By assessing a biomarker profile and/or monitoring the profile in one or more trimesters of pregnancy, the skilled artisan can detect any abnormalities in the inflammatory or anti-inflammatory processes that are occurring. As such, the methods and compositions of the invention are useful to identify or to aid in the identification of women who are at risk of developing a complication during pregnancy, such as preeclampsia, before the complication develops or occurs. In some embodiments, the methods and compositions described herein make it possible to assess the risk a woman will develop a pregnancy complication(s), such as IUGR, preterm labor, and/or recurrent spontaneous abortion.

The biological environment of the developing embryo can be assessed by detecting the serum levels of various biomarkers in one or more of the first, second, and third trimesters of normal pregnant females (pregnancies in which a pregnancy complication does not occur). Applicants assessed the serum level of various biomarkers in the first, second, and third trimesters of pregnant women whose pregnancies were not destined to be complicated by preeclampsia and pregnant women who subsequently developed preeclampsia (referred to interchangeably herein as "prediseased"). For example, biomarker levels were detected in serum samples from pregnant women who were not preeclamptic at the time the sample was collected. The pregnancies of these pregnant women were subsequently tracked to determine which women, if any, developed preeclampsia. The serum that had been collected from pregnant women who did not subsequently develop preeclampsia served as the normal controls for determining biomarker levels. The serum that had been collected from pregnant women who subsequently did develop preeclampsia during the second or third trimester is referred to as "prediseased".

The term "preeclampsia" includes a hypertensive, multi-system disorder of pregnant women, characterized by hypertension, proteinuria, and edema. The most common symptoms of preeclampsia are high blood pressure, increased protein in the urine, and swelling or edema of hands and face. In certain embodiments of the present invention, preeclampsia is defined as hypertension (systolic blood pressure ≧140 mmHg or diastolic blood pressure ≧90 mmHg on at least two occasions, 6 hours apart) and proteinuria (>300 milligrams in a 24 hour urine collection or one dipstick measurement >2+).

In certain embodiments, the invention relates to identifying or aiding in the identification of a pregnant woman at risk of developing preeclampsia. For example, by comparing the serum levels of one or a panel of biomarkers from a pregnant woman in her first trimester of pregnancy to a predetermined standard of the corresponding one or panel of biomarkers for the first trimester of pregnancy, differences in the level(s) of one or more biomarkers can be detected. The level(s) of one or more biomarkers in serum from the pregnant woman can be assessed and compared with one or more biomarkers between the pregnant woman's serum and the predetermined standard to determine whether the pregnant woman is at risk or not at risk of developing preeclampsia. In some embodiments, additional serum samples from the pregnant woman can be taken later in the course of her pregnancy and compared to a predetermined standard for the appropriate trimester, e.g., to a panel of biomarkers for the second trimester if the pregnant woman to be assessed for risk of developing preeclampsia is in her second trimester of pregnancy or to a panel of biomarkers for the third trimester if the pregnant woman to be assessed for risk of developing preeclampsia is in her third trimester of pregnancy.

In some embodiments, the instant invention relates to a predetermined standard that comprises known concentrations of specific biomarkers for each trimester of a normal pregnancy. For example, in certain embodiments, a predetermined standard comprises a known serum concentration range for each of the proteins ANG, leptin, RANTES, PDGF, ICAM 1, VEGF, G-CSF, soluble Fas, EGF, IFGBP 1, MCP 1, IL 8, and FasL that is specific for the first trimester of pregnancy in a healthy subject. In further embodiments, the serum concentration of ANG, leptin, RANTES, PDGF, ICAM 1, VEGF, G-CSF, soluble Fas, EGF, IFGBP 1, MCP 1, IL 8, and FasL in a pregnant woman in her first trimester is compared to this predetermined standard. In yet other embodiments, the methods of the subject invention provide a diagnostic test wherein statistically significant increased serum concentrations of ANG, leptin, RANTES, PDGF, ICAM 1, VEGF, G-CSF, and soluble Fas and statistically significant decreased serum concentrations of EGF, IFGBP 1, MCP 1, IL 8, and FasL are diagnostic of (indicative of) a pregnant woman at risk of developing preeclampsia. In certain embodiments, an increase in the levels of at least two biomarkers selected from the group consisting of ANG, leptin, RANTES, PDGF, ICAM 1, VEGF, G-CSF, and soluble Fas is diagnostic of a pregnant woman at risk of developing preeclampsia. In other embodiments, a decrease in at least two biomarkers selected from the group consisting of EGF, IFGBP 1, MCP 1, IL 8, and/or FasL is diagnostic of a pregnant woman at risk of developing preeclampsia. In yet other embodiments, an increase in at least one biomarker selected from the group consisting of ANG, leptin, RANTES, PDGF, ICAM 1, VEGF, G-CSF, and soluble Fas and a decrease in at least one biomarker selected from the group consisting of EGF, IFGBP 1, MCP 1, IL 8, and FasL are diagnostic of a pregnant woman at risk of developing preeclampsia.

Other non-limiting examples of biomarkers that can be assessed for statistically significant changes in expression include IFNg, I-309, GM-CSF, GDNF, GCP-2, Fraktalkine, Flt-3 Ligand, FGF-7, FGF-6, Eotaxin-3, Eotaxin-2, Eotaxin, CNTF, CK b 8-1, BMP-6, BMP-4, BLC, BDNF, LIGHT, IL-7, IL-6, IL-5, IL-4, IL-3, IL-2, IL-1ra, IL-1b, IL-1a, IL-16, IL-15, IL-13, IL-10, IGF-1, IGFBP-4, IGFBP-2, TNFB, TNFA, TGF-B3, TGF-B1, TARC, SDF-1, SCF, PDGF-BB, PARC, NT-3, NAP-2, MIP-3A, MIP-1D, MIG, MDC, M-CSF, MCP-4, MCP-3, MCP-2, Lymphotactin, I-TAC, IL-6R, IL-1 Ra, IL-17, IL-12 P70, IL-12 P40, IL-11, IL-1R1, IL-1 R4/ST2, IGF-1SR, IGFBP-6, IGFBP-3, ICAM-3, HGF, HCC-4, GRO-A, GRO, VEGF-D, uPAR, TRAIL R4, TRAIL R3, Thrombopoietin, TIMP-2, TIMP-1, TECK, sTNF RI, sTNF RII, SGP130, PIGF, Oncostatin M, Steoprotegin, NT-4, MSP-A, MIP-3B, MIP-1B, MIP-1A, MIF, Fas, FasL, and tissue factor.

In some embodiments, the methods of the invention employ trophoblast cells. In certain embodiments, the trophoblast cells are immortalized trophoblast cells. For example, immortalized trophoblast cells for use in the methods of the subject invention include H8 trophoblast cells. Cells used in the invention can be cultured under standard conditions known in the art (e.g., baseline conditions as described in the Examples). In certain embodiments, trophoblast cells used in the invention are cultured under conditions as provided in the Examples.

The present invention provides methods for the detection of pregnant women at risk of developing preeclampsia as well as methods for the detection of pregnant women with preeclampsia. The subject invention is useful to assess or to aid in the assessment of, for a woman in need thereof, the risk of developing preeclampsia or whether, for a pregnant woman in need thereof, a woman has preeclampsia.

In some embodiments, serum or plasma obtained from a pregnant woman is assessed by the methods of the present invention. In certain embodiments of the present invention, serum or plasma is obtained from a pregnant woman once during the course of the pregnancy. Optionally, serum or plasma is obtained from a pregnant woman more than once during the course of the pregnancy. The serum or plasma for use in embodiments of the subject invention may be obtained from a pregnant woman during the first, second, or third trimester of pregnancy or any combination thereof (e.g., first and second trimesters; e.g., first and third trimesters; e.g., second and third trimesters; e.g., first, second and third trimesters).

In certain embodiments of the invention, trophoblast cells are contacted with serum or plasma obtained from a pregnant woman, e.g., by culturing trophoblast cells in the presence of serum or plasma obtained from a pregnant woman.

The present invention also relates to assessing the viability of trophoblast cells, which is useful to determine if a woman has or is at risk of developing preeclampsia. Cell viability can be assessed by any means known in the art. For example, cell viability may be assessed by a cell proliferation assay such as the CellTiter 96® AQueous One Solution Cell Proliferation Assay (Promega, Madison, Wis.). This assay is a calorimetric method for determining the number of viable cells in proliferation, cytotoxicity or chemosensitivity assays. The CellTiter 96® AQueous One Solution Reagent contains a tetrazolium compound [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine ethosulfate; PES). Assays are performed by adding a small amount of the CellTiter 96® AQueous One Solution Reagent directly to culture wells, incubating for 1-4 hours and then recording absorbance at 490 nm with a 96-well plate reader. The quantity of formazan product as measured by the amount of 490 nm absorbance is directly proportional to the number of living cells in culture.

The present invention further relates to assessing whether trophoblast cells undergo apoptosis. One apoptosis assay that may be used in embodiments of the subject invention is a caspase-3 assay, in which caspase-3 activity is measured using a calorimetric substrate. For example, cleavage of the substrate Ac-DEVD-pNA by caspase-3 releases pNA (p-nitroaniline), which produces a yellow color that can be monitored by a spectrophotometer at 405 nm. The amount of yellow color produced upon cleavage is proportional to the amount of caspase-3 activity.

In certain embodiments of the present invention, apoptosis of trophoblast cells is determined by detection of an apoptotic marker. An apoptotic marker or indicator can be, for example, radioactive molecules, fluorescent molecules, and enzymatic molecules that are associated with apoptotic cell death. For example, apoptotic markers include active caspase-3, e.g., caspase-3 p17 and p19 fragments. Another apoptosis assay that may be used to assess trophoblast cell death is the TUNEL assay, which is used to detect the presence of apoptotic cell death. In the TUNEL assay, the enzyme terminal deoxynucleotidyl transferase labels 3'-OH DNA ends (which are generated during apoptosis) with biotinylated nucleotides. The biotinylated nucleotides are then detected by immunoperoxidase staining. In further embodiments, apoptotic features such as cell shrinkage, chromatin condensation, and DNA fragmentation may be detected as indicators of apoptosis.

Apoptosis is an adaptive process which balances cell growth and death to maintain tissue homeostasis. Many genes are involved in the control of apoptosis. The Fas/Fas Ligand (Fas/FasL) system is one of the main apoptotic pathways. The Fas/FasL system is expressed in immune as well as non-immune cells such as trophoblasts (50). Its expression and function responds to changes in the microenvironment, playing a pivotal role in controlling cell proliferation and tissue remodeling (22, 23). Both FasL and Fas are transmembranous proteins of the TNF-α/TNFα-receptor family. The binding of the Fas receptor by FasL results in a downstream activation of a cascade of intracellular proteolytic enzymes ending in apoptosis (51).

Although cytotrophoblast cells from normal pregnancies express Fas and FasL, they are resistant to Fas mediated apoptosis (19, 52). Furthermore, it has been demonstrated that this resistance to Fas-mediated apoptosis is in part dependent on the cytokine profile at the implantation site (19). Applicants hypothesize that changes in the normal microenvironment at the implantation site may influence trophoblast sensitivity to apoptosis, which may then lead to placental damage, impaired trophoblast invasion and pathological conditions such as preeclampsia.

In certain embodiments, the present invention relates to a cytotoxic assay comprising trophoblast cells treated with sera from women with normal pregnancies and pregnancies complicated by preeclampsia. Further, Applicants have demonstrated a differential effect of sera from preeclamptic patients and normal patients on trophoblast cell viability and sensitivity to Fas-mediated apoptosis.

Lately, attention has turned to the role of apoptosis in normal tissue remodeling of the female reproductive tract and the effect of excessive apoptosis in degenerative diseases such as preeclampsia, IUGR and preterm labor (12, 13). Apoptosis within the pregnant uterus is important for the establishment of immune privilege, as well as the regulation of placental growth (14, 15). However, excessive trophoblast apoptosis may affect placental function, resulting in adverse perinatal outcome. Increased trophoblast apoptosis has been documented in the placenta of growth-restricted fetuses (16), recurrent spontaneous abortion (17), preeclamptic pregnancy, and post-term pregnancy (18). The balance between cell proliferation and cell death is determined by factors produced at the maternal-fetal interface or by the maternal circulation (19).

Another area of study has focused on the importance of the trophoblast in the pathophysiology of preeclampsia. Specifically, deportation of villous trophoblast debris directly into the maternal circulation (39, 40, 41) has been implicated in the genesis of the exaggerated intravascular maternal inflammatory response noted in patients with preeclampsia. In addition, increased apoptosis of villous and extra villous trophoblasts has been reported in cases of preeclampsia (42, 43).

Applicants suggest that there is a link between maternal serum factors and trophoblast apoptosis. Applicants have demonstrated that serum from women with preeclampsia increases trophoblast sensitivity to Fas-mediated apoptosis (20) and increases the release of microvesicles containing tissue factor. Although the magnitude is different, the effect on trophoblast cell viability observed in active pre-eclamptic cases is similar to that seen when trophoblast cells are exposed to the "pre-disease" sera. Interestingly, the "pre-disease" sera induced a greater decrease in cell viability than the decrease in viability induced by sera from women with active disease. Hence, instead of a pressor agent being responsible for the initiation of preeclampsia, as previously believed, other factor(s), such as pro-inflammatory cytokine(s), may initiate an abnormally high rate of trophoblast apoptosis (44).

This increased trophoblast apoptosis and increased release of microvesicles containing tissue factor may in turn lead to defective placental function. It has been shown that the pro-inflammatory cytokines TNF-α and IFN-γ increase trophoblast sensitivity to apoptotic stimuli, whereas anti-inflammatory cytokines, including IL-10, protect trophoblast cells from apoptosis by up-regulating anti-apoptotic proteins such as FLIP (14, 19). Work described herein indicates a role for apoptosis in the pathophysiology of trophoblast diseases such as preeclampsia and IUGR. A significant decrease in trophoblast viability was observed with sera from women who subsequently developed preeclampsia (24% vs. 4% p=0.013) and was associated with caspase-3 activation. Accordingly, factors capable of inducing trophoblast apoptosis are present in the patients' sera weeks or months before the clinical development of the disease. The invention described herein is useful to identify women at risk of preeclampsia.

In one embodiment of the present invention, the invention relates to the study of apoptosis in preeclampsia as a marker for the onset of the disease. In one embodiment, the present invention can be utilized as a sensitive assay to screen for patients at risk of developing preeclampsia. In certain embodiments, the sensitivity of this assay is 81%, and the specificity 66%, wherein a "positive test" is defined by a reduction in trophoblast viability greater than 10%. In one embodiment, a pregnant woman is diagnosed as being at risk of developing preeclampsia when there is a greater than 10% reduction in trophoblast viability as assessed by the methods of the present invention. For example, in certain embodiments, if there is a greater than 10% reduction in viability of trophoblast cells cultured in the presence of serum from a pregnant woman when compared to the viability of trophoblast cells cultured in the absence of serum from the pregnant woman, then the woman is determined to be at risk for developing preeclampsia. By assessing large numbers of patients, the sensitivity and specificity of the assays of the subject invention can be increased.

An advantage of the present invention is the fact that its use is not limited to the third trimester. The methods of the present invention can be used in any trimester, including early in pregnancy, for example, the first trimester. It is useful earlier in a woman's pregnancy to predict or aid in predicting the likelihood that a woman will develop preeclampsia. For example, Applicants showed differential effects of sera obtained as early as 6 weeks of gestation on trophoblast cell viability. A reduction in trophoblast viability was observed in the pre-disease group, regardless of the trimester in which the serum sample was obtained.

Results described herein support a link between serum factor(s) and trophoblast viability. This factor(s) may be responsible for changes in the normal microenvironment at the implantation site, which may have a direct effect on trophoblast viability, leading to impaired trophoblast function and invasion. Regardless of the specific nature of this factor (s), it appears that it is present and active several weeks before pregnant women show clinical signs/symptoms of preeclampsia.

The articles "a," "an" and "the" are used herein to refer to one or to more than one (to at least one) of the grammatical object of the article.

The term "including" is used herein to mean, and is used interchangeably with, the phrase "including but not limited to".

The term "such as" is used herein to mean, and is used interchangeably with, the phrase "such as but not limited to".

II. Methods of Diagnosis

Expression of a biomarker that is useful in a method of the present invention may be assessed by any of a wide variety of well known methods for detecting expression of a transcribed molecule or its corresponding protein. Non-limiting examples of such methods include immunological methods for detection of secreted proteins, protein purification methods, protein function or activity assays, nucleic acid hybridization methods, nucleic acid reverse transcription methods, and nucleic acid amplification methods. In one embodiment, expression of a biomarker is assessed using an antibody (e.g., a radio-labeled, chromophore-labeled, fluorophore-labeled, or enzyme-labeled antibody), an antibody derivative (e.g., an antibody conjugated with a substrate or with the protein or ligand of a protein-ligand pair, such as biotin-streptavidin), or an antibody fragment (e.g., a single-chain antibody or an isolated antibody hypervariable domain) which binds specifically with a protein corresponding to a biomarker, such as the protein encoded by the open reading frame corresponding to a marker gene or such a protein that has undergone all or a portion of its normal post-translational modification. In another embodiment, expression of a biomarker is assessed by preparing mRNA and/or cDNA (a transcribed polynucleotide) from cells in a sample obtained from a pregnant woman, and by hybridizing the mRNA and/or cDNA with a reference polynucleotide that is a complement of a polynucleotide comprising the biomarker, and fragments thereof. cDNA can, optionally, be amplified using any of a variety of polymerase chain reaction methods prior to hybridization with the reference polynucleotide.

In yet other embodiments, the expression of one or more biomarkers is detected by detecting the expression of a polypeptide which is regulated by the one or more biomarker; detecting the expression of a polypeptide which regulates said biomarker; or detecting the expression of a metabolite of said biomarker.

As used herein, the term "ANG" includes all homologs, naturally occurring allelic variants, isoforms and precursors of ANG. ANG is also known as Angiogenin, ribonuclease A family, 5 and RNAse 5. In one embodiment, angiogenin comprises the amino acid sequence of GenBank Accession No. NP_001136.

As used herein, the term "leptin" includes all homologs, naturally occurring allelic variants, isoforms and precursors of leptin. Leptin is also known as HGNC:6553, OB, OBS, obesity, or murine obesity homolog. In one embodiment, leptin comprises the amino acid sequence of GenBank Accession No. NP_000221.

As used herein, the term "RANTES" includes all homologs, naturally occurring allelic variants, isoforms and precursors of RANTES. RANTES is also known as Regulated Upon Activation, Normally T-Expressed, and Presumably Secreted; chemokine, CC motif, ligand 5; CCL5; Small Indicible Cytokine A5; SCYA5; T Cell-Specific RANTES; T Cell-Specific Protein p228; and TCP228. In one embodiment, RANTES comprises the amino acid sequence of GenBank Accession No. NP_002976.

As used herein, the term "PDGF" includes all homologs, naturally occurring allelic variants, isoforms and precursors of PDGF. PDGF is also known as Platelet-Derived Growth Factor. In one embodiment, PDGF comprises the amino acid sequence of GenBank Accession No. NP_148937.

As used herein, the term "ICAM 1" includes all homologs, naturally occurring allelic variants, isoforms and precursors of ICAM 1. ICAM 1 is also known as Intercellular Adhesion Molecule 1, CD54, Surface Antigen of Activated B Cells, BB2; BB2; antigen identified by monoclonal antibody BB2. In one embodiment, ICAM 1 comprises the amino acid sequence of GenBank Accession No. NP_000192.

As used herein, the term "VEGF" includes all homologs, naturally occurring allelic variants, isoforms and precursors of VEGF. VEGF is also known as Vascular Endothelial Growth Factor. In one embodiment, VEGF comprises the amino acid sequence of GenBank Accession No. NP_001020537.

As used herein, the term "G-CSF" includes all homologs, naturally occurring allelic variants, isoforms and precursors of G-CSF. G-CSF is also known as Granulocyte Colony-Stimulating Factor; Colony-Stimulating Factor 3; and CSF3. In one embodiment, G-CSF comprises the amino acid sequence of GenBank Accession No. NP_000750.

As used herein, the term "Fas" includes all homologs, naturally occurring allelic variants, isoforms and precursors of Fas. Fas is also known as tumor necrosis factor receptor superfamily, member 6; TNFRSF6; apoptosis antigen 1; APT1; surface antigen APO1; APO1; and CD95. In one embodiment, Fas comprises the amino acid sequence of GenBank Accession No. NP_000034.

As used herein, the term "FasL" includes all homologs, naturally occurring allelic variants, isoforms and precursors of FasL. FasL is also known as Fas ligand; tumor necrosis factor ligand superfamily, member 6; TNFSF6; apoptosis antigen ligand 1; APTILG1; apoptosis antigen ligand; CD95 ligand; CD95L; CD178 antigen; and CD178. In one embodiment, FasL comprises the amino acid sequence of GenBank Accession No. NP_000630.

As used herein, the term "EGF" includes all homologs, naturally occurring allelic variants, isoforms and precursors of EGF. EGF is also known as Epidermal Growth Factor; urogastrone; URG. In one embodiment, EGF comprises the amino acid sequence of GenBank Accession No. NP_001954.

As used herein, the term "IGFBP 1" includes all homologs, naturally occurring allelic variants, isoforms and precursors of IGFBP 1. IGFBP 1 is also known as insulin-like growth factor-binding protein 1; IBP 1; placental protein 12; and IGF-BP25. In one embodiment, IGFBP 1 comprises the amino acid sequence of GenBank Accession No. NP_000587.

As used herein, the term "MCP 1" includes all homologs, naturally occurring allelic variants, isoforms and precursors of MCP 1. MCP 1 is also known as monocyte chemotactic protein 1; monocyte chemotactic and activating factor; MCAF; small inducible cytokine A2; and SCYA2. In one embodiment, MCP 1 comprises the amino acid sequence of GenBank Accession No. NP_002973.

As used herein, the term "IL 8" includes all homologs, naturally occurring allelic variants, isoforms and precursors of IL 8. IL 8 is also known as Interleukin 8; small inducible cytokine subfamily b, member 8; SCYB8; monocyte-derived neutrophil chemotactic factor; neutrophil-activating peptide 1; NAP 1; granulocyte chemotactic protein 1; GCP1; CXC chemokine ligand 8; and CXCL8. In one embodiment, IL 8 comprises the amino acid sequence of GenBank Accession No. NP_000575.

As used herein, the term "sample" refers to a material obtained from a female. The sample can be derived from any biological source, including body fluids (such as, for example, whole blood, plasma, serum, saliva, ocular lens fluid, sweat, urine, milk, etc.), tissue or extracts, cells, etc.

III. Kits

In some embodiments, the instant invention provides kits relating to the methods and/or compositions of the invention.

Reagents may be labeled compounds or agents useful to detect a polypeptide or an mRNA encoding a polypeptide corresponding to a biomarker of the invention in a biological sample and means for determining the amount of the polypeptide or mRNA in the sample (e.g., an antibody that binds the polypeptide or an oligonucleotide probe that binds to DNA or mRNA encoding the polypeptide). Suitable reagents for binding with a polypeptide corresponding to a biomarker useful in a method of the subject invention include antibodies, antibody derivatives, antibody fragments, and the like. Suitable reagents for binding with a nucleic acid (e.g. a genomic DNA, an mRNA, a spliced mRNA, a cDNA, or the like) include complementary nucleic acids.

For antibody-based kits, the kit can comprise, for example: (1) a first antibody (e.g., attached to a solid support) which binds to a polypeptide corresponding to a biomarker of the invention; and, optionally, (2) a second, different antibody that binds to either the polypeptide or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a polypeptide corresponding to a biomarker of the invention or (2) a pair of primers useful for amplifying a nucleic acid molecule corresponding to a biomarker of the invention.

The reference sample is used to compare the results obtained from the sample being tested.

The kit can also comprise other components such as a buffering agent, a preservative, or a protein stabilizing agent. The kit can further comprise components necessary for detecting the detectable label (e.g., an enzyme or a substrate).

Each component of the kit can be enclosed within an individual container and all of the various containers can be within a single package, along with instructions for interpreting the results of the assays performed using the kit.

In another embodiment, the kits of the invention comprise trophoblast cells, media suitable for culturing trophoblast cells, and containers for carrying out the methods of the present invention. Containers that may be employed in the subject invention include any container suitable for carrying out the invention, for example, a container suitable for use in the present invention is a well such as a microtiter-plate well. In certain embodiments, the kits of the invention include instructions for carrying out the present invention.

IV. Screening Methods

The present invention also relates to methods to screen for candidate compounds useful to treat a pregnancy complication, such as preeclampsia.

As used herein, the term "compound" refers to any chemical entity, pharmaceutical, drug, and the like that can be used to treat or prevent a disease, illness, condition, or disorder of bodily function. Compounds comprise both known and potential therapeutic compounds. A compound can be determined to be therapeutic by screening using the screening methods of the present invention. Examples of test compounds include, but are not limited to, peptides, polypeptides, synthetic organic molecules, naturally occurring organic molecules, nucleic acid molecules, and combinations thereof.

In certain embodiments, a method of identifying a compound useful to treat preeclampsia comprises (a) identifying a candidate compound which regulates the expression of one or more biomarkers selected from the group consisting of: Ang, Leptin, RANTES, PDGF, ICAM 1, VEGF, G-CSF, Fas, EGF, IGFBP 1, MCP 1, IL8, and FasL; and (b) determining whether such candidate compound is effective to treat preeclampsia, wherein if the candidate compound is effective to treat preeclampsia, a compound useful to treat preeclampsia is identified. In some embodiments, the method is useful to identify a candidate compound that regulates the expression of two or more biomarkers.

The above described screening methods can be used to screen for candidate compounds useful to treat preeclampsia.

The invention also comprises a method to screen for candidate biomarkers indicative of a risk of developing preeclampsia ("preeclampsia risk" biomarkers) comprising: (i) identifying a group of biomarkers that may be associated with preeclampsia (such as cytokines and growth factors); (ii) comparing the level of expression of the biomarkers identified in step (i) in a first population of subjects at risk of developing preeclampsia ("preeclampsia risk" subjects) and in healthy subjects; (iii) selecting biomarkers exhibiting a significant difference in expression in the first population of preeclampsia risk subjects; (iv) comparing the level of expression of the biomarkers identified in step (iii) in a second population of preeclampsia risk subjects and in healthy subjects; and (v) selecting biomarkers exhibiting a significant difference in expression in the second population of preeclampsia risk subjects, wherein the biomarkers identified in step (v) are candidate preeclampsia risk biomarkers. The first population of preeclampsia risk subjects and the second population of preeclampsia risk subjects may be any two preeclampsia risk populations so long as the two populations are different. Such biomarkers can be selected from the group consisting of cytokines and growth factors.

In one embodiment, the method further comprises: (vi) comparing the level of expression of the biomarkers identified in step (v) in a third population of preeclampsia risk subjects and in healthy subjects, wherein the expression of the biomarkers is detected by using a different assay format; and (vi) selecting biomarkers exhibiting a significant different in expression in the third population of preeclampsia risk patients; wherein the biomarkers identified in step (vii) are candidate biomarkers for preeclampsia. Thus, for example, in one embodiment, the expression of the biomarker is first detected using a high throughput assay, and then detected using an assay that is specific for the protein in question. For example, in one embodiment, the expression of the biomarker is first detected by using a microarray immunoassay and then detected by Luminex and/or by ELISA assay. The third population of preeclampsia risk subjects may be the same or different from the first and second population of preeclampsia risk subjects.

In one embodiment, the method further comprises determining whether the biomarkers identified in step (v) or (vii) can distinguish between preeclampsia risk and healthy subjects in a blind study. The results of the blind study can be analyzed using well known statistical methods.

The expression of the biomarkers can be compared using any method known in the art. In one embodiment, the expression of the biomarkers is detected using protein array, mass spectroscopy, gel electrophoresis or an immunoassay. In one embodiment, the expression of the biomarkers is detected using microarray immunoassay. In another embodiment, the expression of the biomarkers is measured using Luminex. In yet another embodiment, the expression of the biomarkers is measured using ELISA. These methods are well known in the art.

The invention also comprises a method to screen for candidate preeclampsia risk biomarkers comprising: (i) identifying a preeclampsia risk biomarker; (ii) selecting polypeptides which regulate or are regulated by the biomarker identified in step (i); and (iii) measuring the expression of the polypeptides identified in step (ii) in preeclampsia risk subjects and in healthy subjects, wherein a polypeptide which is differentially expressed in preeclampsia risk subjects and in healthy subjects is a candidate preeclampsia risk biomarker.

Preeclampsia risk subjects can be selected, for example, based on risk factors such as family history, first pregnancy, and the like. Also, preeclampsia risk subjects can be selected based on blood samples obtained from stored samples, such as for example, blood samples collected retrospectively as part of a regular screening of the general population of patients as well as those at risk of developing preeclampsia.

The practice of the present invention will employ, unless otherwise indicated, conventional techniques of cell biology, cell culture, molecular biology, microbiology, recombinant DNA, and immunology, which are within the skill of the art. Such techniques are described in the literature. See, for example, Current Protocols in Cell Biology, ed. by Bonifacino, Dasso, Lippincott-Schwartz, Harford, and Yamada, John Wiley and Sons, Inc., New York, 1999.

VI. Business Methods

The invention further comprises a method of conducting a business comprising: (i) obtaining a sample; (ii) detecting the expression of at least one biomarker in the sample, wherein said one or more biomarker is selected from the group consisting of the biomarkers identified in Table 2; and (iii) reporting the results of such detection. In one embodiment, the one or more biomarkers are selected from the group consisting of the biomarkers identified in Table 3. In another embodiment, the one or more biomarkers are selected from the group consisting of ANG, Leptin, RANTES, PDGF, ICAM 1, VEGF, G-CSF, Fas, EGF, IGFBP 1, MCP 1, IL8, and FasL.

The invention further comprises a method of conducting a business comprising: (i) obtaining a sample; (ii) detecting the expression of ANG, Leptin, RANTES, PDGF, ICAM 1, VEGF, G-CSF, Fas, EGF, IGFBP 1, MCP 1, IL8, and FasL; and (iii) reporting the results of such detection.

EXEMPLIFICATION

The invention now being generally described, it will be more readily understood by reference to the following examples, which are included merely for purposes of illustration of certain aspects and embodiments of the present invention, and are not intended to limit the invention.

Example 1

Trimester-specific Biomarker Detection in Normal and Prediseased Pregnant Women

Blood Samples

Serum samples were obtained from 27 pregnant women. Twenty samples were obtained from women who remained normotensive throughout the gestation (herein referred to as normal). Seven samples were from women who were normotensive at the time that the serum samples were obtained and who subsequently developed preeclampsia (herein referred to as pre-diseased). Preeclampsia was defined as hypertension (systolic blood pressure $\geq 140$ mmHg or diastolic blood pressure $\geq 90$ mmHg on at least two occasions, 6 hours apart) and proteinuria (>300 milligrams in a 24 hour urine collection or one dipstick measurement >2+). Blood samples were obtained from normal and prediseased patients in the first, second, and third trimester. Pregnancies were considered normal when medical and obstetrical complications of pregnancy were ruled out and birthweight was appropriate-for-gestational-age at term ($\geq 37$ gestational weeks). At the time each sample was collected, it was not known whether the patient would develop preeclampsia. All samples were evaluated in a blind manner, and the correlation with pregnancy output was done at the end of the study.

The medical records of all of the normal control patients were reviewed to confirm that none of them had antepartum, intrapartum or postpartum complications. Patients with chronic hypertension, diabetes mellitus, antiphospholipid antibody syndrome, or a known chronic medical disease were excluded. The use of these samples for research purposes was approved by the Human Investigation Committee at Yale University and the NICHD IRB.

The patient characteristics relating to the data presented in FIGS. 1-14 is shown in Table 1 below.

TABLE 1

Maternal Demographics
MATERNAL DEMOGRAPHICS

|  | NORMOTENSIVE | PRE-DISEASED |
|---|---|---|
| Number of patients | 20 | 7 |
| Mean maternal age (yrs) | 23.7 | 24.1 |
| Gravida (mean) | 2.29 | 1.97 |
| Mean gestational age at blood draw (wks) | 8 | 10.1 |
| Nulliparous (number) | 5 | 3 |

Proteins used to screen for biomarkers of the first, second, and/or third trimesters of a normal pregnancy and for biomarkers of pregnancies destined to be complicated by preeclampsia are presented in Tables 2 and 3 below. See also, for example, FIGS. 2-4. As used herein, the term "analyte" refers to a molecule or compound, such as a polypeptide or nucleic acid, whose presence is to be identified in a sample.

TABLE 2

Array VI analytes

| | Protein (abbr.) | Protein (full name) |
|---|---|---|
| 1 | ANG | Angiogenin |
| 2 | BDNF | Brain-derived neurotrophic factor |
| 3 | BLC | B-lymphocyte chemoattractant |
| 4 | BMP-4 | Bone morphogenetic protein 4 |
| 5 | BMP-6 | Bone morphogenetic protein 6 |
| 6 | CK b 8-1 | CK b 8-1 |
| 7 | CNTF | Ciliary neurotrophic factor |
| 8 | EGF | Epidermal growth factor |
| 9 | Eotaxin | Eotaxin |
| 10 | Eotaxin-2 | Eotaxin-2 |
| 11 | Eotaxin-3 | Eotaxin-3 |
| 12 | Flt-3 Lig | fms-like tyrosine kinase-3 ligand |
| 13 | FGF-6 | Fibroblast growth factor-6 |
| 14 | FGF-7 | Fibroblast growth factor-7 |
| 15 | Fractalkine | Fractalkine |
| 16 | GCP-2 | Granulocyte chemotactic protein 2 |
| 17 | GDNF | Glial cell line derived neurotrophic factor |
| 18 | GM-CSF | Granulocyte macrophage colony stimulating factor |
| 19 | I-309 | I-309 |
| 20 | IFN-γ | Interferon gamma |
| 21 | IGFBP-1 | Insulin-like growth factor binding protein 1 |
| 22 | IGFBP-2 | Insulin-like growth factor binding protein 2 |
| 23 | IGFBP-4 | Insulin-like growth factor binding protein 4 |
| 24 | IGF-1 | Insulin-like growth factor 1 |
| 25 | IL-10 | Interleukin 10 |
| 26 | IL-13 | Interleukin 13 |
| 27 | IL-15 | Interleukin 15 |
| 28 | IL-16 | Interleukin 16 |
| 29 | IL-1α | Interleukin 1 alpha |

TABLE 2-continued

Array VI analytes

| Protein (abbr.) | Protein (full name) |
| --- | --- |
| 30 IL-1β | Interleukin 1 beta |
| 31 IL-1ra | Interleukin 1 receptor antagonist |
| 32 IL-2 | Interleukin 2 |
| 33 IL-3 | Interleukin 3 |
| 34 IL-4 | Interleukin 4 |
| 35 IL-5 | Interleukin 5 |
| 36 IL-6 | Interleukin 6 |
| 37 IL-7 | Interleukin 7 |
| 38 Leptin | Leptin |
| 39 LIGHT | Tumor necrosis factor ligand superfamily, member 14; TNFSF14 |
| 40 MCP-1 | Monocyte chemotactic protein 1 |
| 41 MCP-2 | Monocyte chemotactic protein 2 |
| 42 MCP-3 | Monocyte chemotactic protein 3 |
| 43 MCP-4 | Monocyte chemotactic protein 4 |
| 44 M-CSF | Macrophage colony stimulating factor |
| 45 MDC | Metalloproteinase-like, disintegrin-like, and cysteine-rich protein |
| 46 MIG | Monokine induced by gamma interferon |
| 47 MIP-3α | Macrophage inflammatory protein 3 alpha |
| 48 MIP-1δ | Macrophage inflammatory protein 1 delta |
| 49 NAP-2 | Neutrophil Activating Peptide 2 |
| 50 NT-3 | Neurotrophin 3 |
| 51 PARC | Pulmonary and activation-regulated chemokine |
| 52 PDGF-BB | Platelet-derived growth factor, beta polypeptide |
| 53 RANTES | Regulated upon activation, normal T expressed and presumably secreted |
| 54 SCF | Stem cell factor |
| 55 SDF-1 | Stromal cell-derived factor 1 |
| 56 TARC | Thymus and activation regulated chemokine |
| 57 TGF-B1 | Transforming growth factor, beta-1 |
| 58 TGF-B3 | Transforming growth factor, beta-3 |
| 59 TNF-α | Tumor necrosis factor alpha |
| 60 TNF-β | Tumor necrosis factor beta |

TABLE 3

Array VII analytes

| Protein (abbr.) | Protein (full name) |
| --- | --- |
| 1 GRO | CXCL1 |
| 2 GRO-A | GRO protein, alpha |
| 3 HCC4 (NCC4) | Hemofiltrate CC chemokine 4 |
| 4 HGF | Hepatocyte growth factor |
| 5 ICAM-1 | Intercellular adhesion molecule 1 |
| 6 ICAM-3 (CD50) | Intercellular adhesion molecule 3 |
| 7 IGFBP-3 | Insulin-like growth factor binding protein 3 |
| 8 IGFBP-6 | Insulin-like Growth Factor Binding Protein 6 |
| 9 IGF-1SR | soluble Insulin-like Growth Factor 1 Receptor |
| 10 IL-1 R4/ST2 | Interleukin 1 R4/ST2 |
| 11 IL-1R1 | Interleukin 1 Receptor, Type I |
| 12 IL-11 | Interleukin 11 |
| 13 IL-12 (p40) | Interleukin 12 p40 |
| 14 IL-12 (p70) | Interleukin 12 p70 |
| 15 IL-17 | Interleukin 17 |
| 16 IL-1ra | Interleukin 1 receptor antagonist |
| 17 IL-6R | Interleukin 6 receptor |
| 18 IL-8 | Interleukin 8 |
| 19 I-TAC | Interferon gamma-inducible T cell alpha chemoattractant |
| 20 Lymphotactin | Lymphotactin |
| 21 MIF | Macrophage migration inhibitory factor |
| 22 MIP-1α | Macrophage inflammatory protein 1 alpha |
| 23 MIP-1β | Macrophage inflammatory protein 1 beta |
| 24 MIP-3β | Macrophage inflammatory protein 3 beta |
| 25 MSP-A | Macrophage stimulating protein A |
| 26 NT-4 | Neurotrophin 4 |
| 27 Oncostatin M | Oncostatin M |
| 28 PIGF | Placental growth factor |
| 29 sgp130 | Soluble glycoprotein 130 |
| 30 sTNF RII | soluble Tumor Necrosis Factor Receptor 2 |

TABLE 3-continued

Array VII analytes

| Protein (abbr.) | Protein (full name) |
| --- | --- |
| 31 sTNF RI | soluble Tumor Necrosis Factor Receptor 1 |
| 32 TECK | Thymus-expressed chemokine |
| 33 TIMP-1 | Tissue inhibitors of metalloproteinases 1 |
| 34 TIMP-2 | Tissue inhibitors of metalloproteinases 2 |
| 35 Thrombopoietin | Thrombopoietin |
| 36 TRAIL R3 | TNF-related apoptosis-inducing ligand receptor 3 |
| 37 TRAIL R4 | TNF-related apoptosis-inducing ligand receptor 4 |
| 38 uPAR | Urokinase plasminogen activator receptor |
| 39 VEGF | Vascular endothelial growth factor |
| 40 VEGF-D | Vascular endothelial growth factor D |

The proteins identified in Tables 2 and 3 are also known by other names, which can be identified by reference to the full name of the protein and by reference to the published literature. One way of identifying other names for the proteins identified in Tables 2 and 3 is by reference to the various NCBI databases, which include GenBank.

Figure 2A:
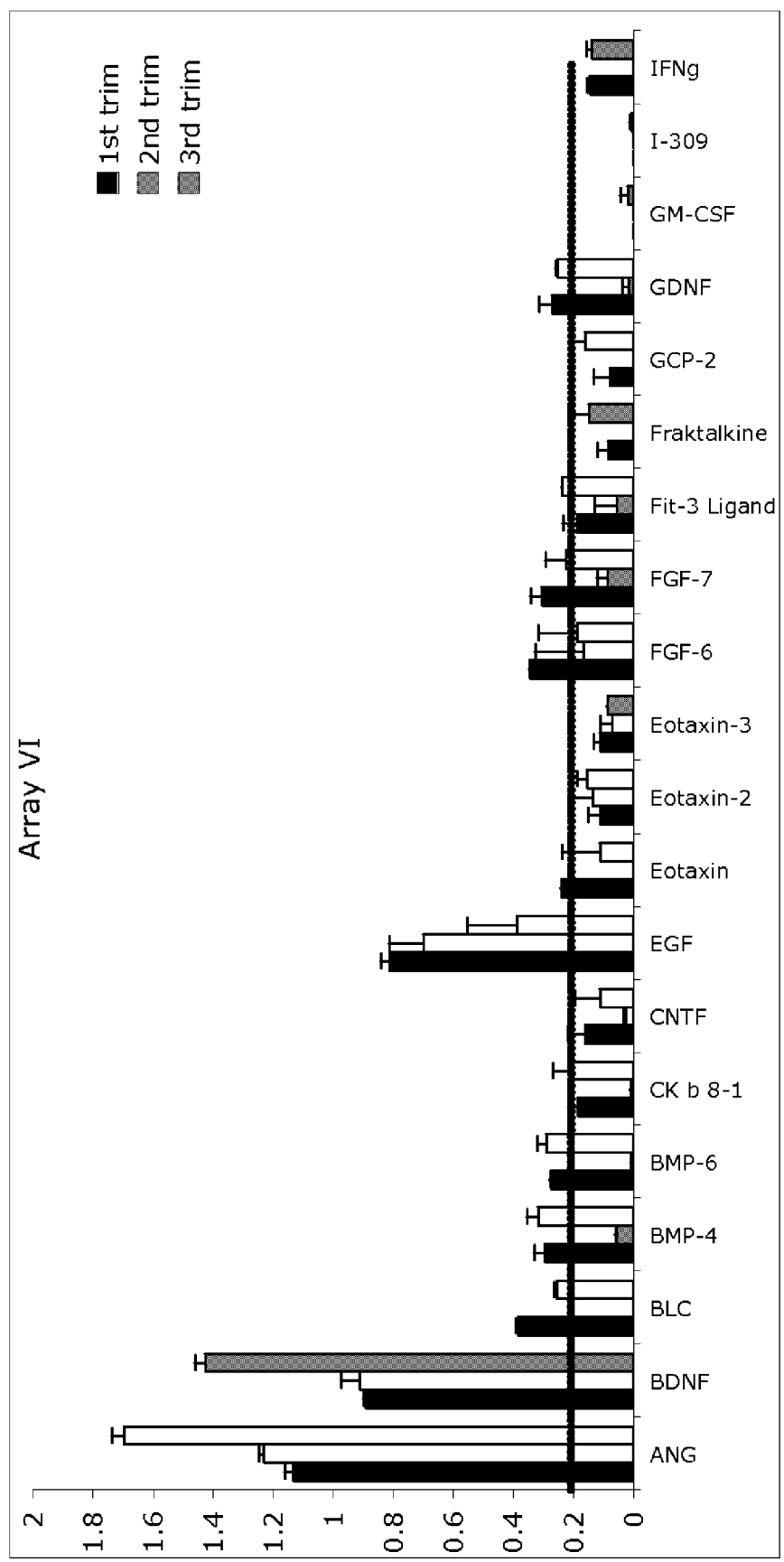
FIGS. 2A-2C are bar graphs depicting the serum levels as assessed by cytokine array of the indicated proteins in the first, second, and third trimesters of a normal pregnancy.
Figure 2B:
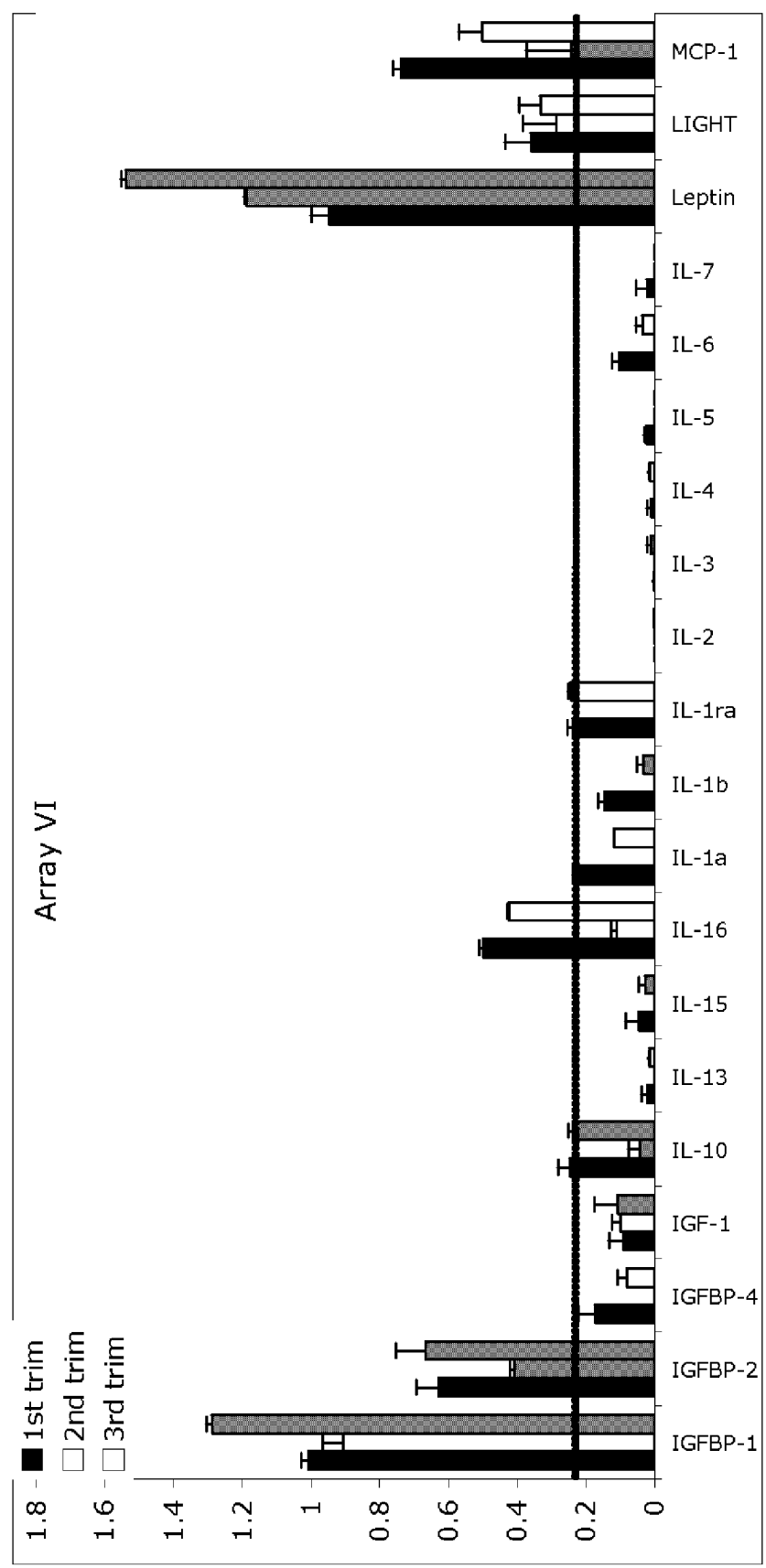
Figure 2C:
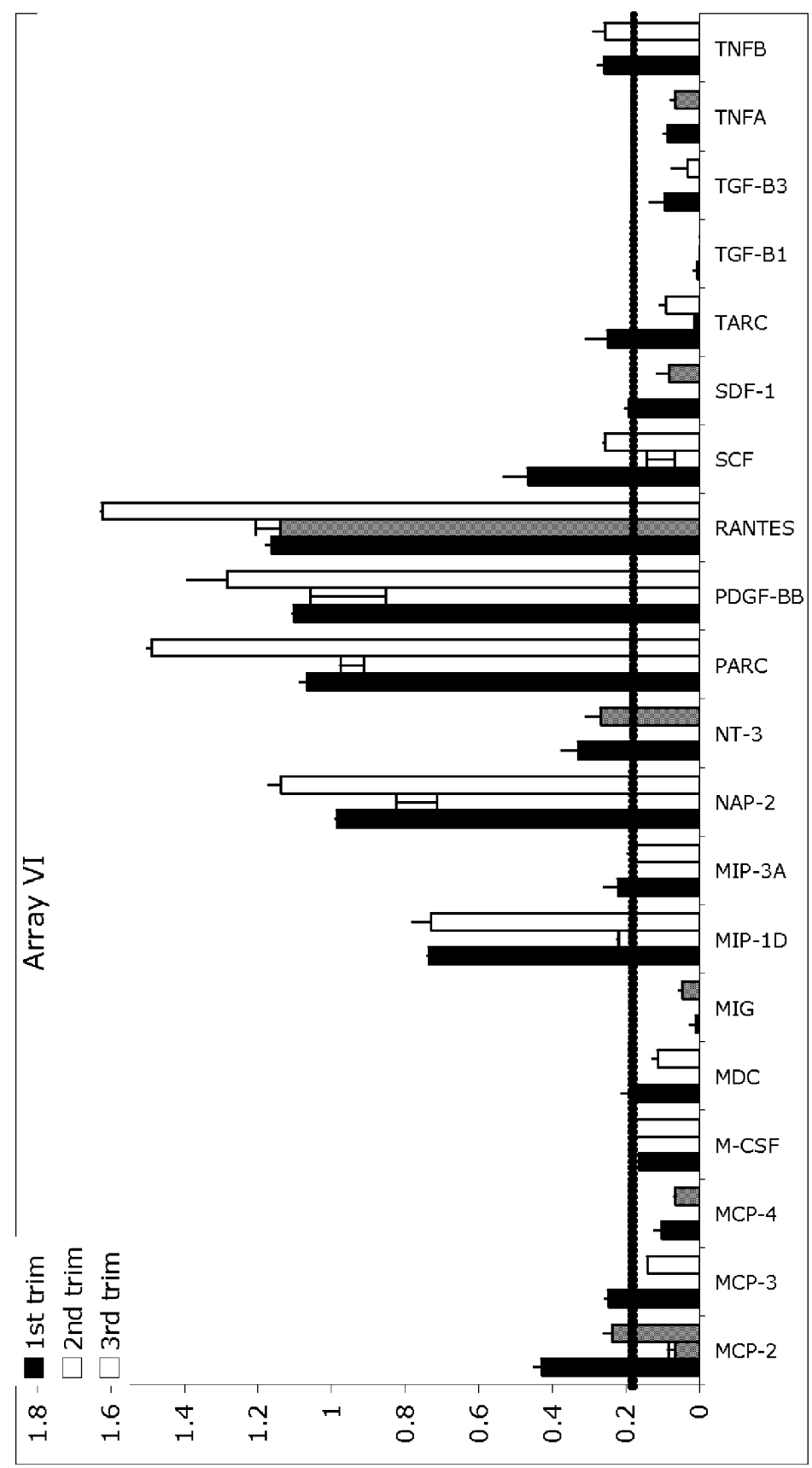
Figure 3A:
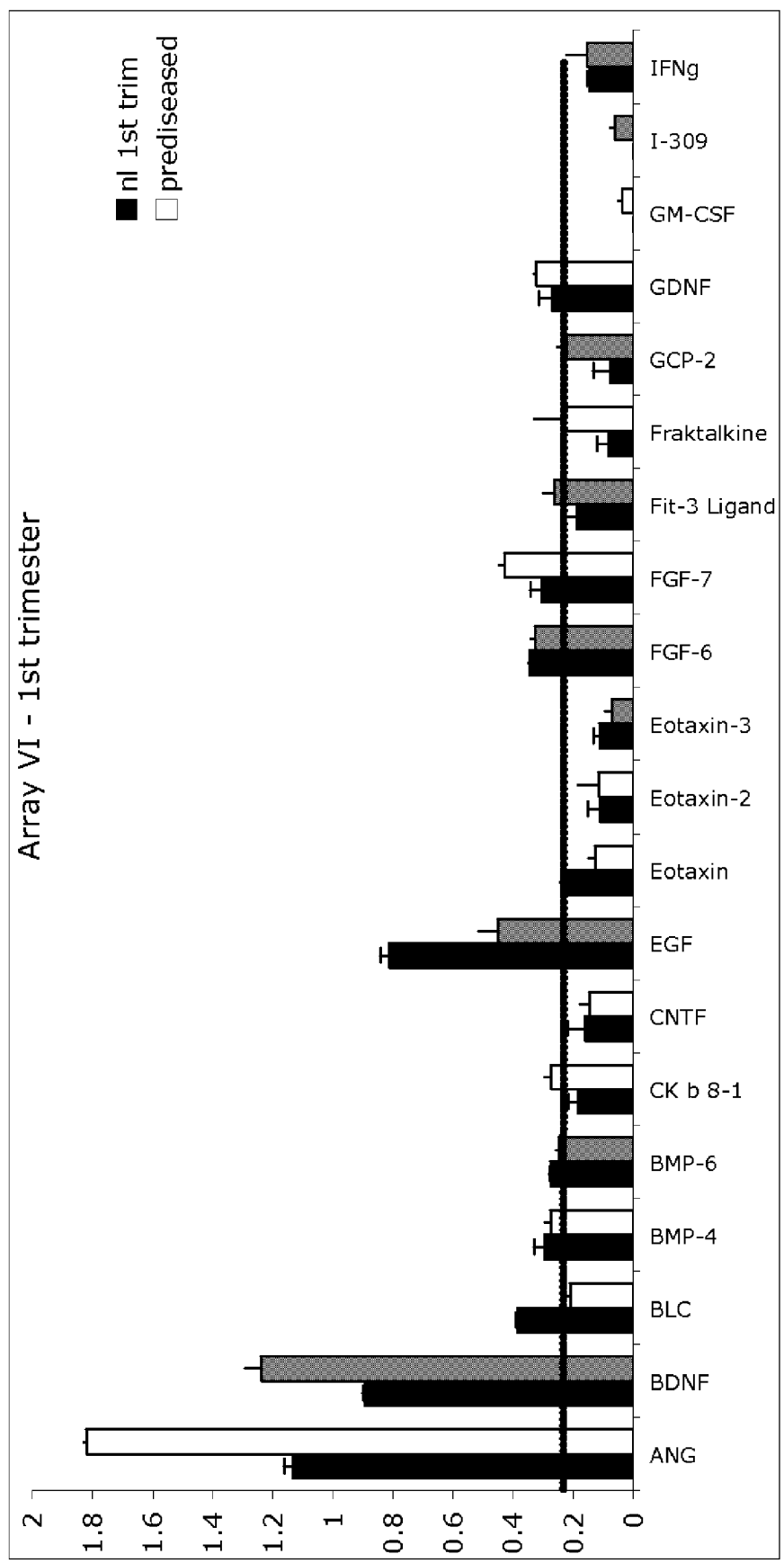
FIGS. 3A-3C are bar graphs depicting the serum levels as assessed by cytokine array of the indicated proteins in the first trimester of a normal pregnancy and pregnancies destined to be complicated by preeclampsia ("prediseased" pregnancies).
Figure 3B:
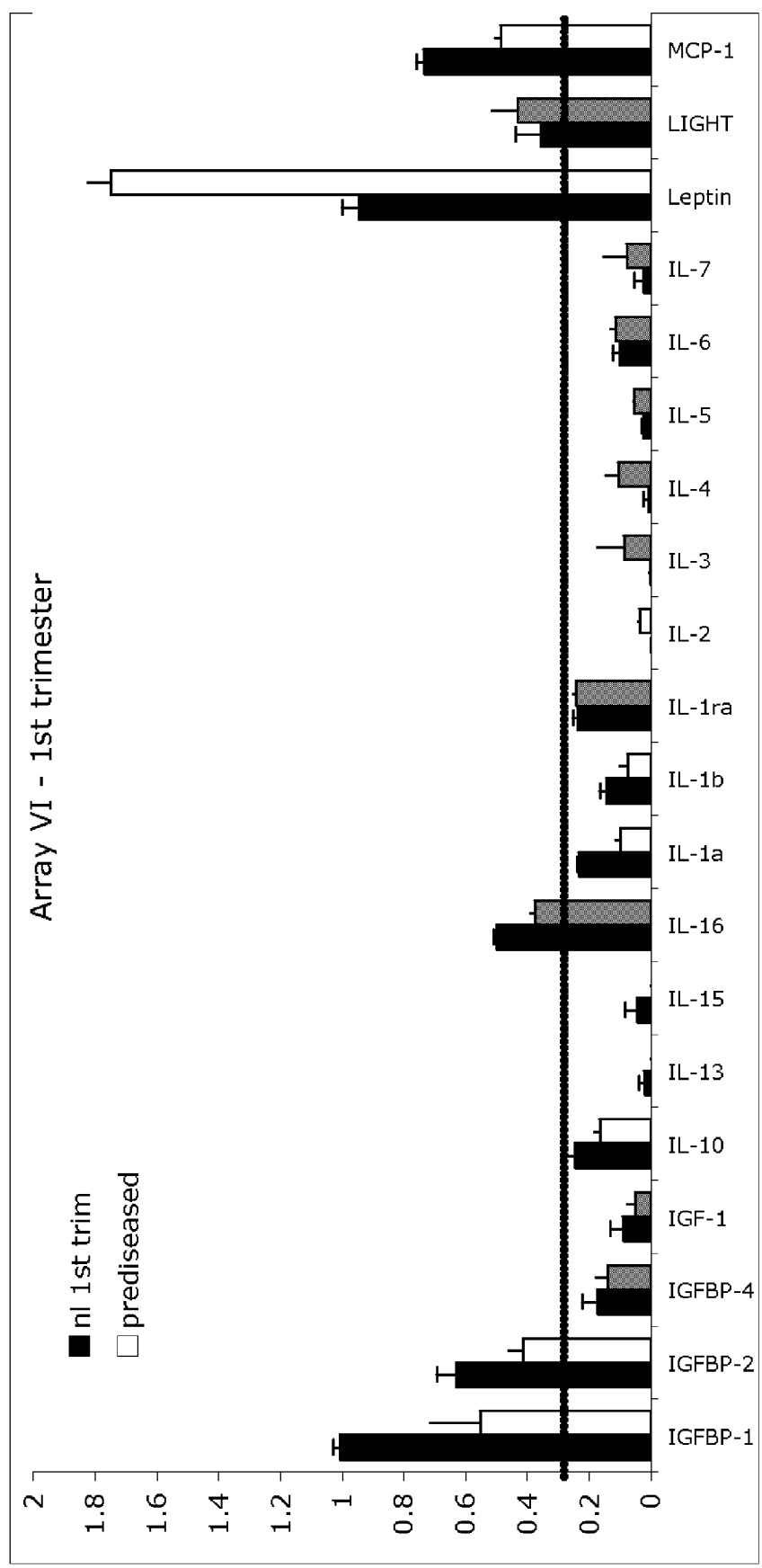
Figure 3C:
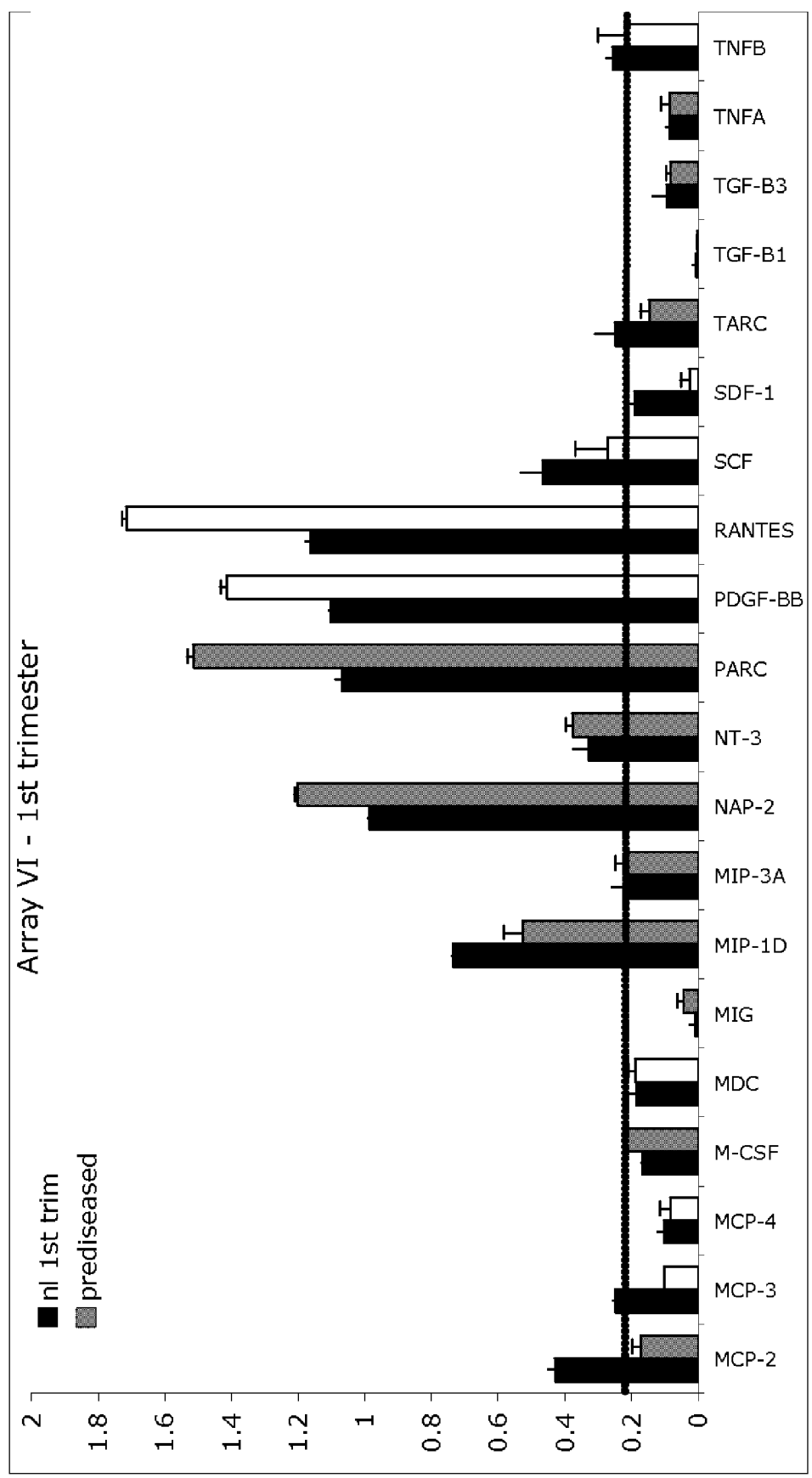
Figure 4A:
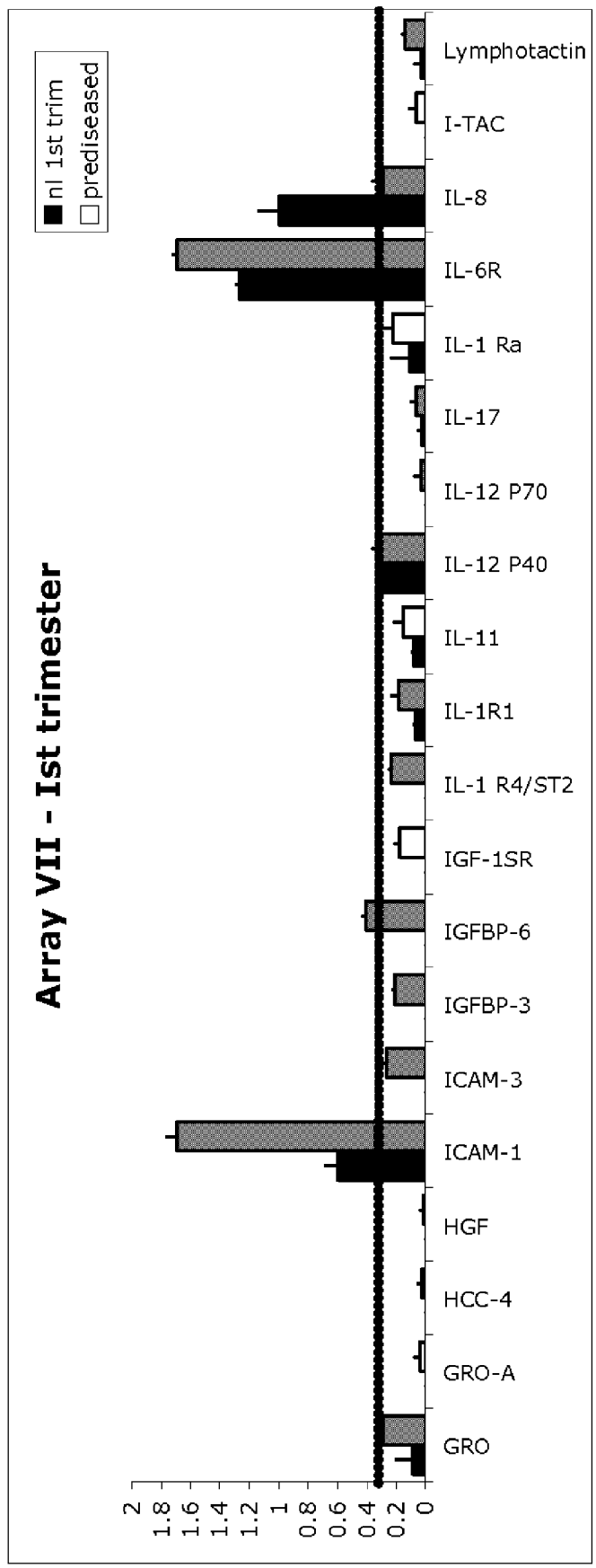
FIGS. 4A-4B are bar graphs depicting the serum levels as assessed by cytokine array of the indicated proteins in the first trimester of normal pregnancy and prediseased pregnancies.
Figure 4B:
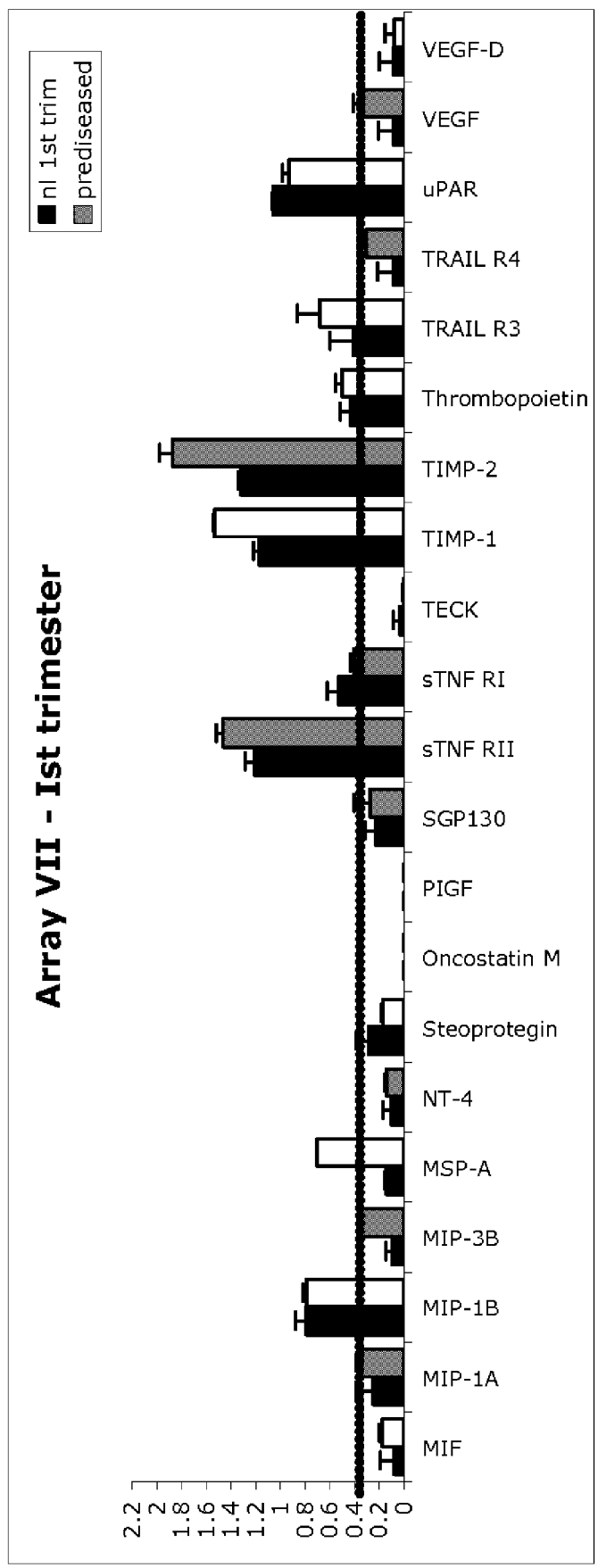

Cytokine Arrays 100 ml of sera from each patient was incubated with the array membrane (RayBiotech, Atlanta, Ga.). A single array was used for each individual sample from an experiment and each experiment was performed twice. Following incubation with primary biotin-conjugated antibodies and HRP-conjugated streptavidin, detection of signals was performed by enhanced chemiluminescence. The intensity of the signals was quantified by densitometry using a digital imaging analysis system and 1D Image Analysis Software (Eastman Kodak Company). The software quantifies the signals and expresses the results as optical density units. The signal intensities were then adjusted for the internal negative controls (background) and then normalized against the internal positive controls on each array membrane, which were given the arbitrary unit of 1. Any expression levels below 0.2 units were considered below the detection limit of the assay, as determined by the software. Results are depicted in FIGS. 2-4.

Luminex® Assays

The use of Luminex® (Luminex Corp., Austin, Tex.), unlike the ELISA assay, allows the use of small sample volume (15-25 μl), and less time for a greater number of samples. This technology permits the simultaneous analysis of up to 100 different biomolecules (such as proteins) in a single microplate well. The Bio-Plex suspension array system uses multiplexing technology that may include up to 100 color-coded bead sets, each of which can be conjugated with a different specific reactant. Each reactant is specific for a different antibody. These reactants are used to create a capture sandwich immunoassay as in ELISA assays. The constituents of each well are drawn up into the flow-based Bio-Plex array reader, which identifies each specific reaction based on bead color and can simultaneously quantitate up to 100 protein targets in culture media, sera, and other matrices, automatically analyze up to 96 samples in under 35 mins and increase the amount of useful data per sample. The assay solution is drawn into the array reader, which illuminates and reads the sample, generates a standard curve and measures the amount of protein in each analyte.

Luminex® assays were conducted on sera of normal and prediseased pregnant women during their first, second, and/or third trimester of pregnancy to determine biomarker serum levels corresponding to normal pregnancy and pregnancy destined to be complicated by preeclampsia. The results of these assays for the indicated biomarkers are presented in FIGS. 5-15. All serum concentrations are in pg/ml for each biomarker, unless otherwise indicated.

Figure 5:
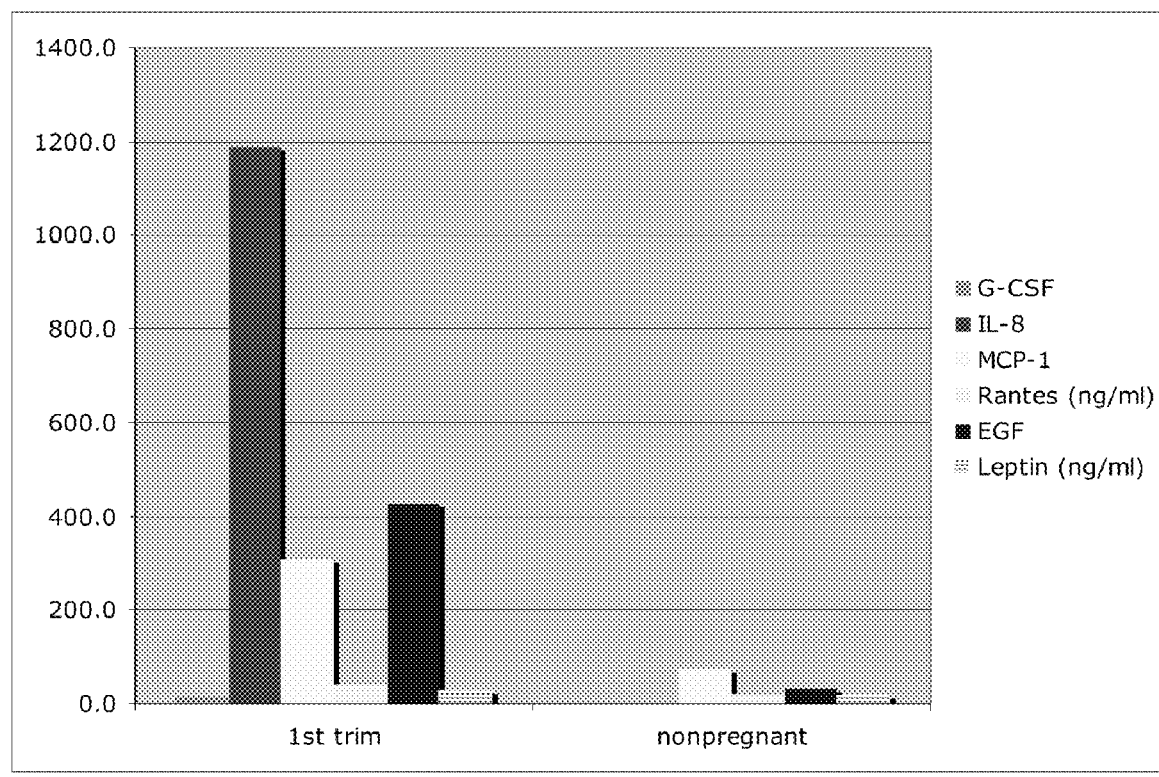
FIG. 5 is a bar graph depicting the serum levels as assessed by Luminex® assays of the indicated proteins in the first trimester of normal pregnancies and in women who are not pregnant.
Figure 6:
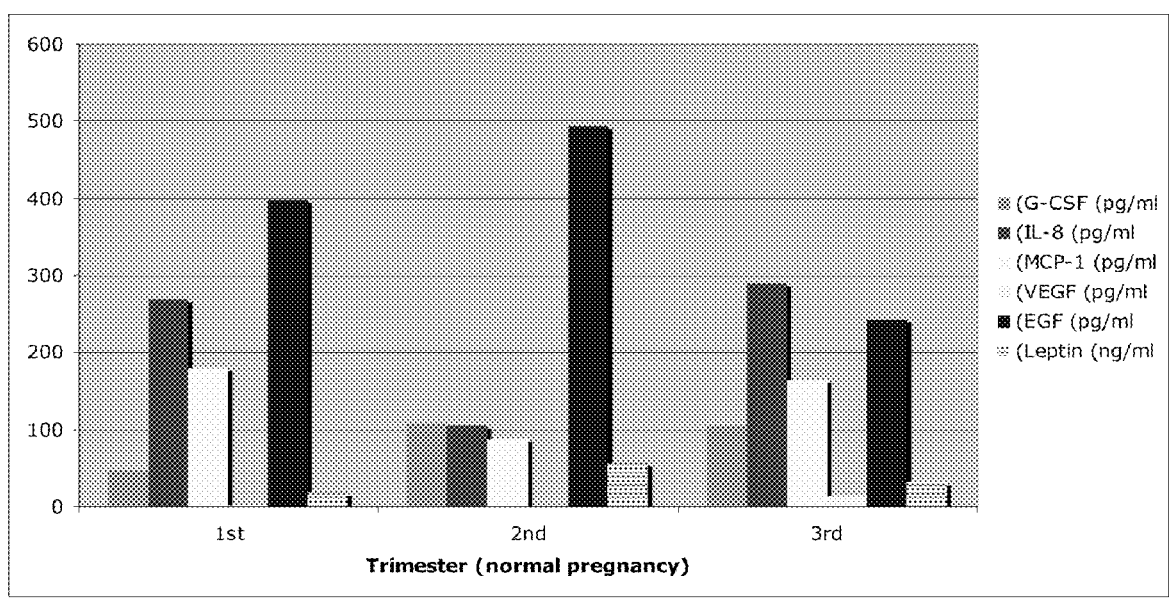
FIG. 6 is a bar graph depicting the serum levels as assessed by Luminex® assays of the indicated proteins in the first, second, and third trimesters of a normal pregnancy.
Figure 7:
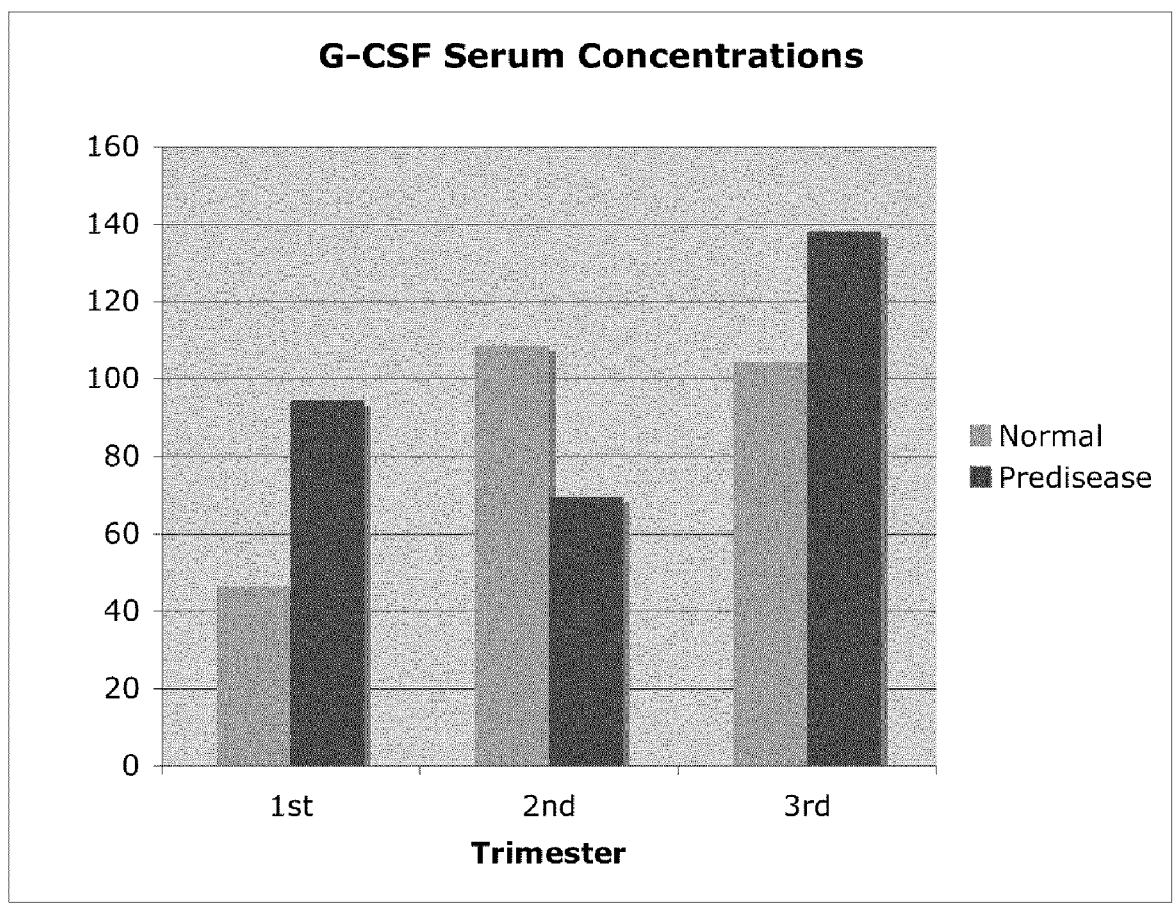
FIG. 7 is a bar graph depicting the serum levels as assessed by Luminex® assays of G-CSF in the first, second, and third trimesters of normal and prediseased pregnancies.
Figure 8:
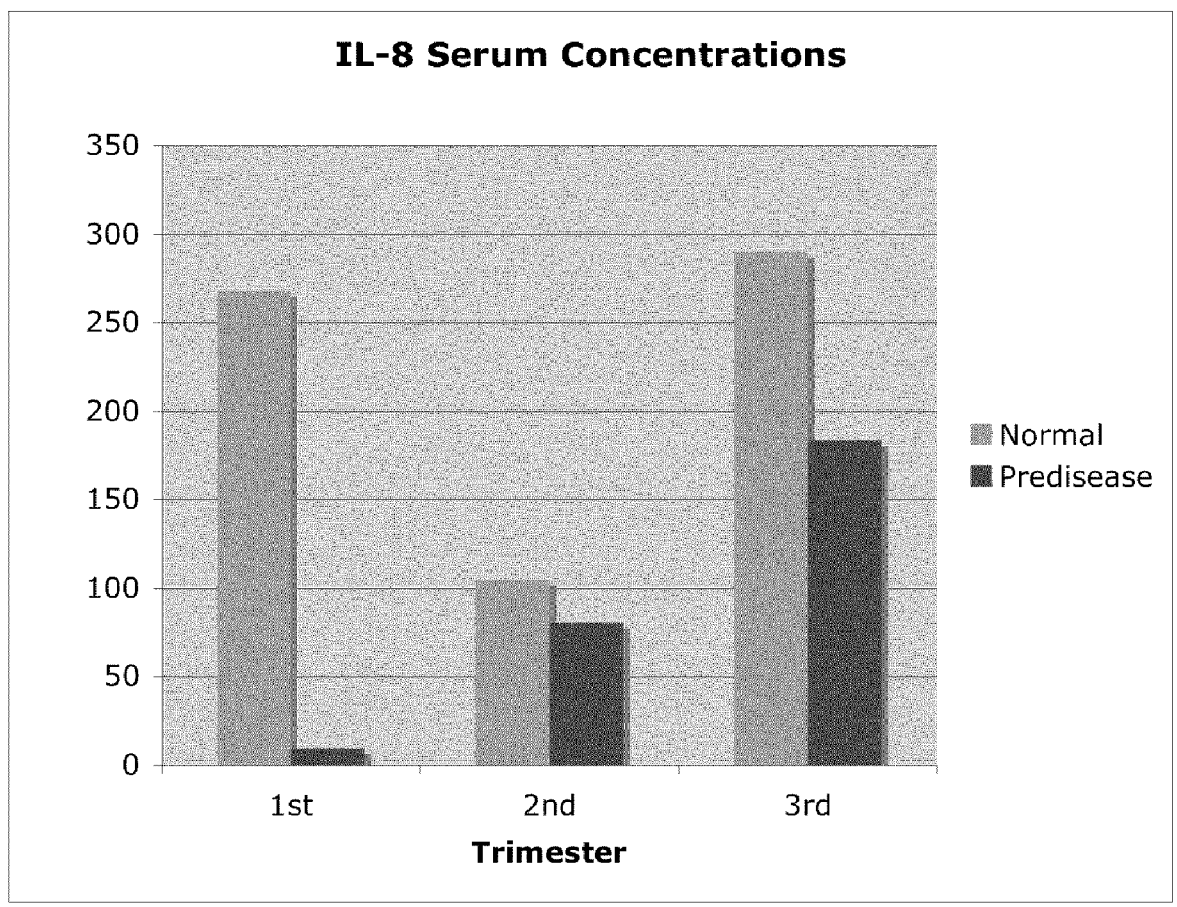
FIG. 8 is a bar graph depicting the serum levels as assessed by Luminex® assays of IL-8 in the first, second, and third trimesters of normal and prediseased pregnancies.
Figure 9:
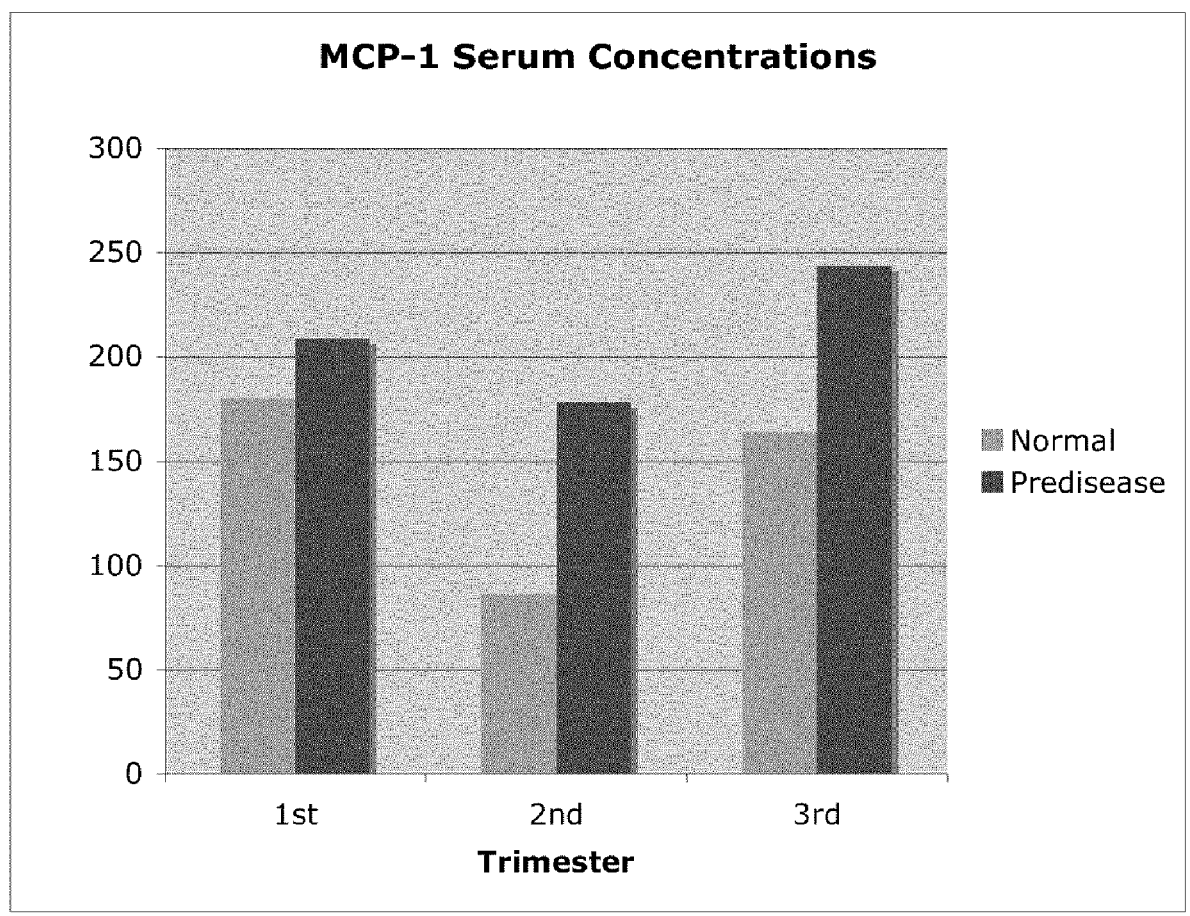
FIG. 9 is a bar graph depicting the serum levels as assessed by Luminex® assays of MCP-1 in the first, second, and third trimesters of normal and prediseased pregnancies.
Figure 10:
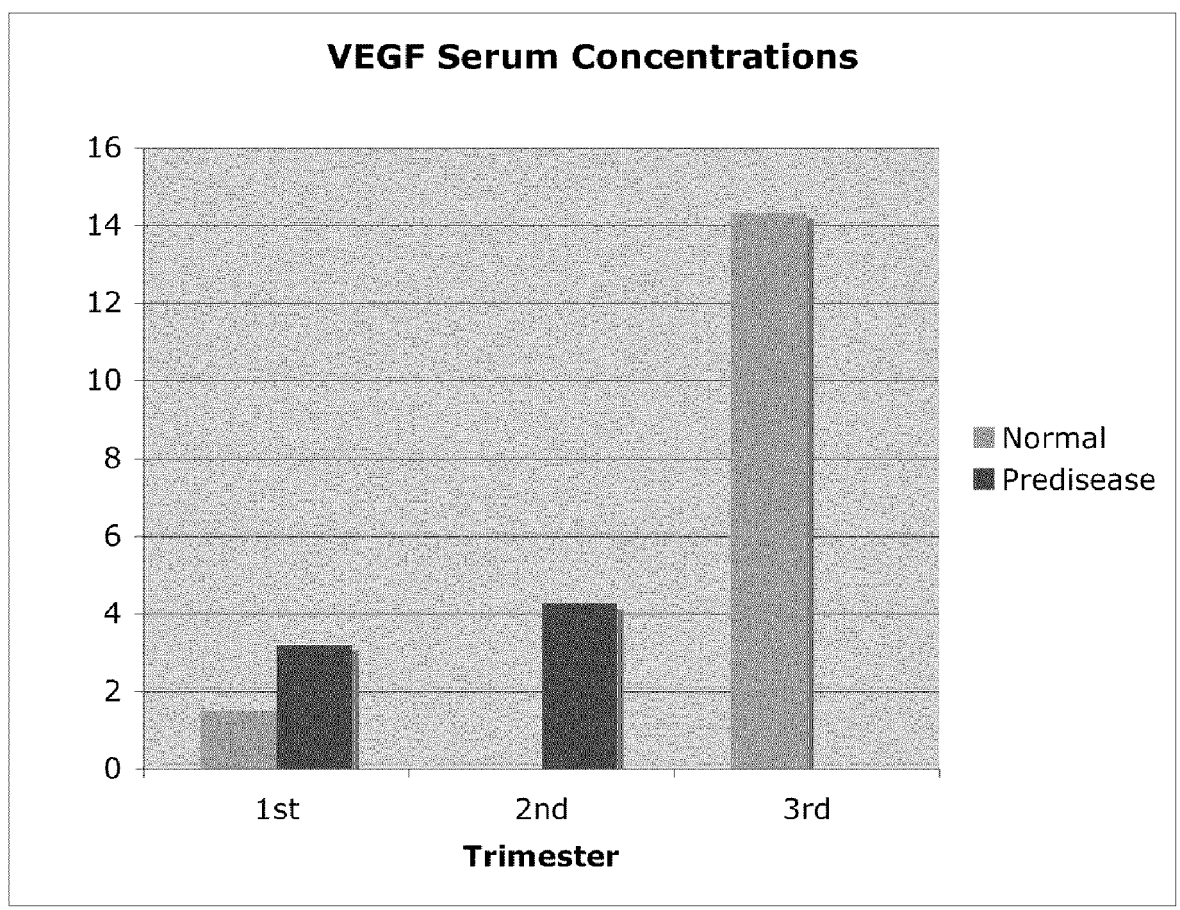
FIG. 10 is a bar graph depicting the serum levels as assessed by Luminex® assays of VEGF in the first, second, and third trimesters of normal and prediseased pregnancies.
Figure 11:
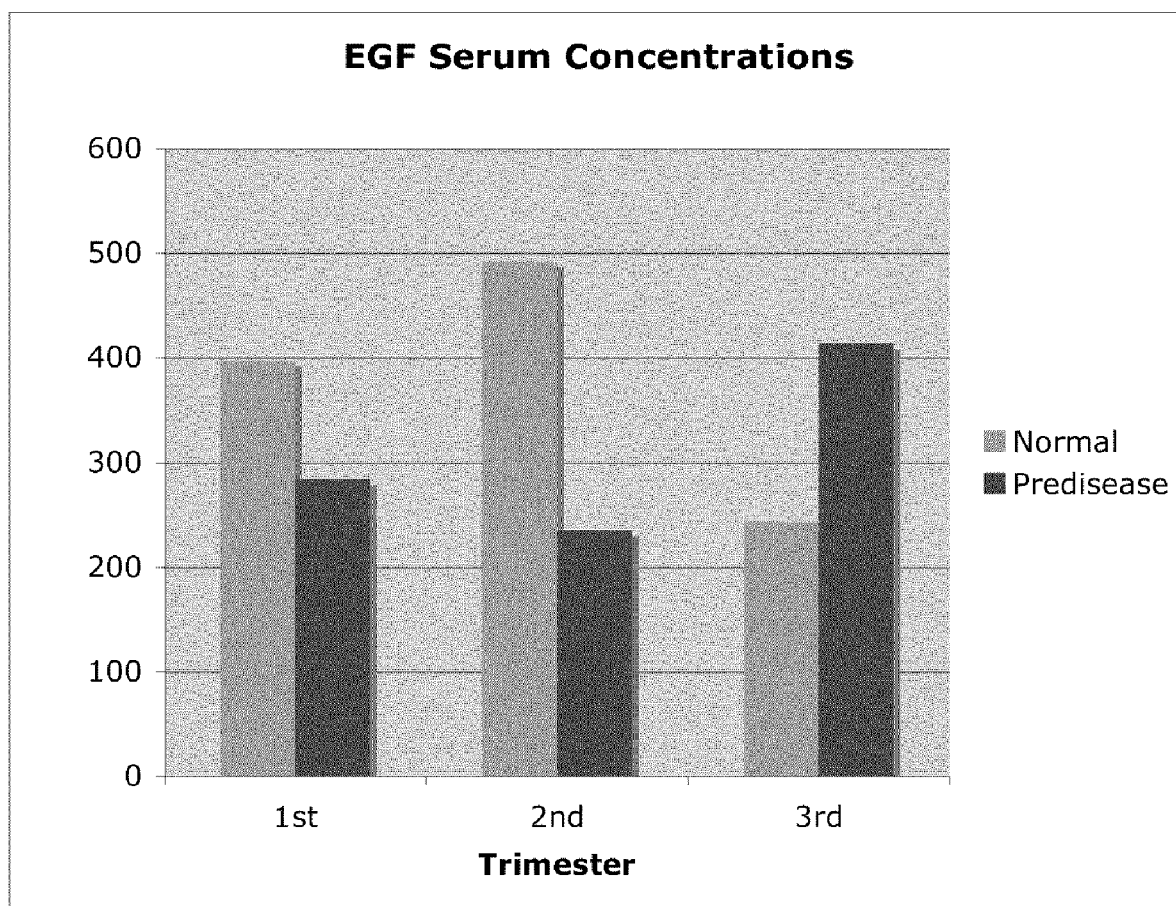
FIG. 11 is a bar graph depicting the serum levels as assessed by Luminex® assays of EGF in the first, second, and third trimesters of normal and prediseased pregnancies.
Figure 12:
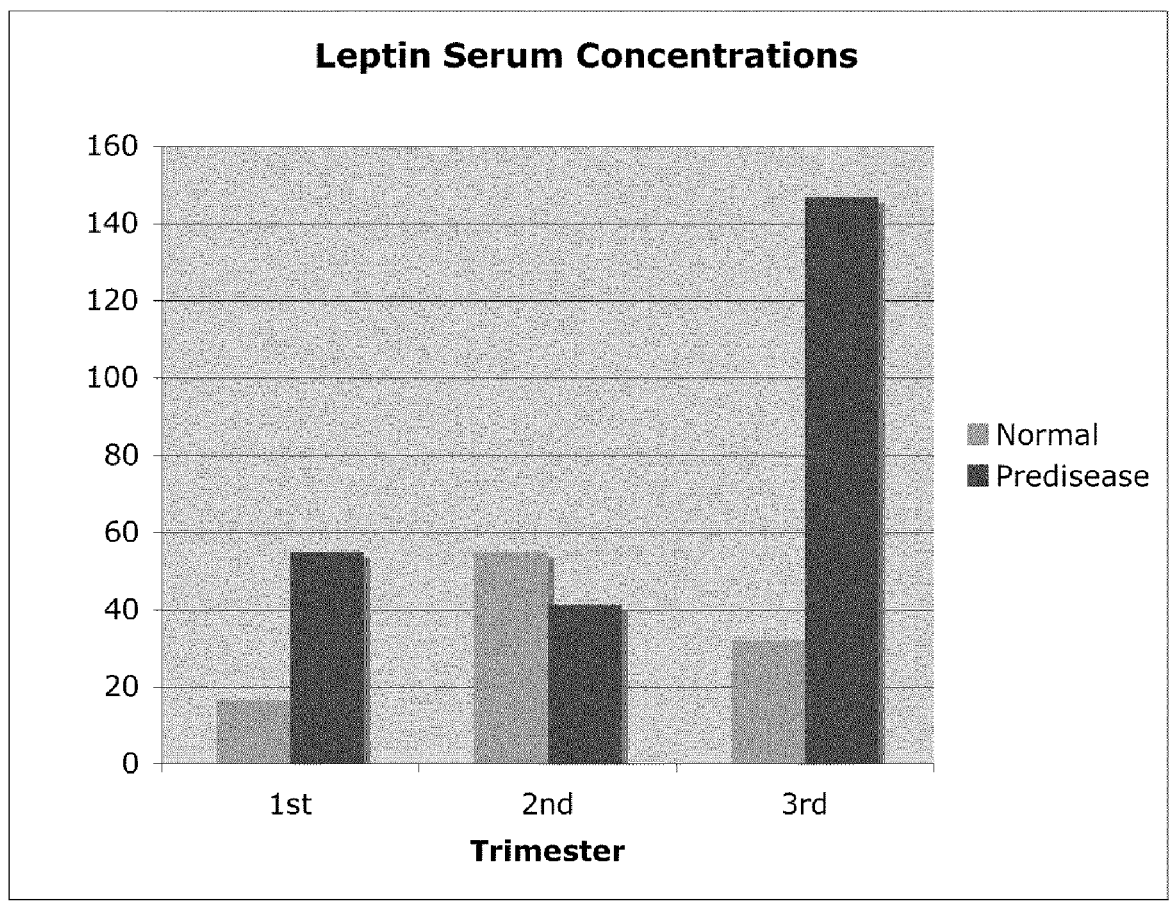
FIG. 12 is a bar graph depicting the serum levels as assessed by Luminex® assays of Leptin in the first, second, and third trimesters of normal and prediseased pregnancies.
Figure 13:
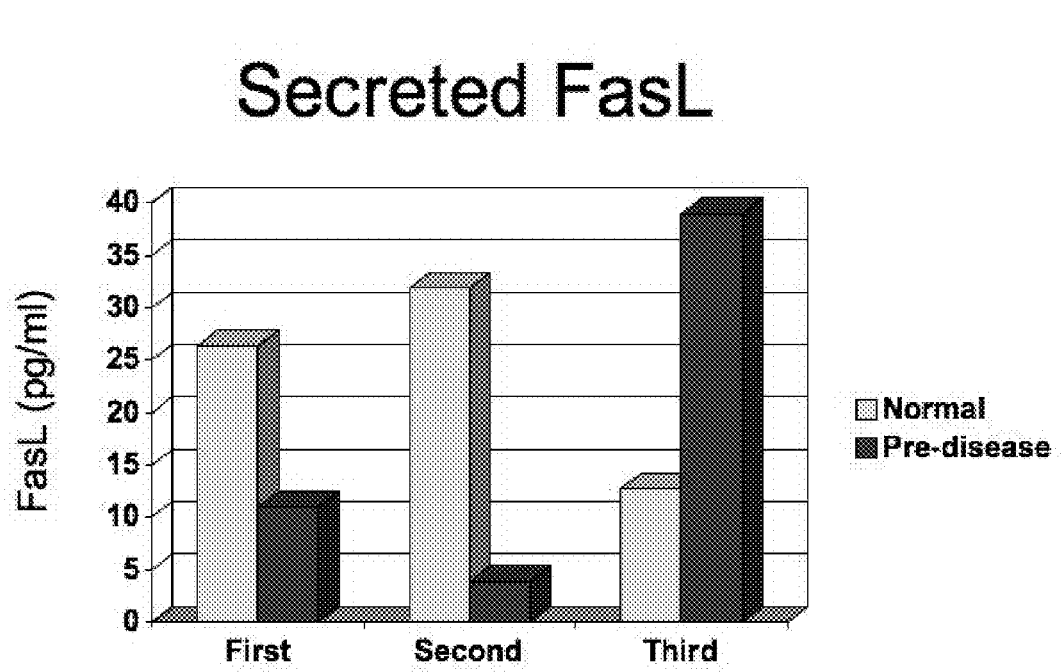
FIG. 13 is a bar graph depicting secreted FasL levels as assessed by Luminex® assays in the first, second, and third trimesters of normal and prediseased pregnancies.
Figure 14:
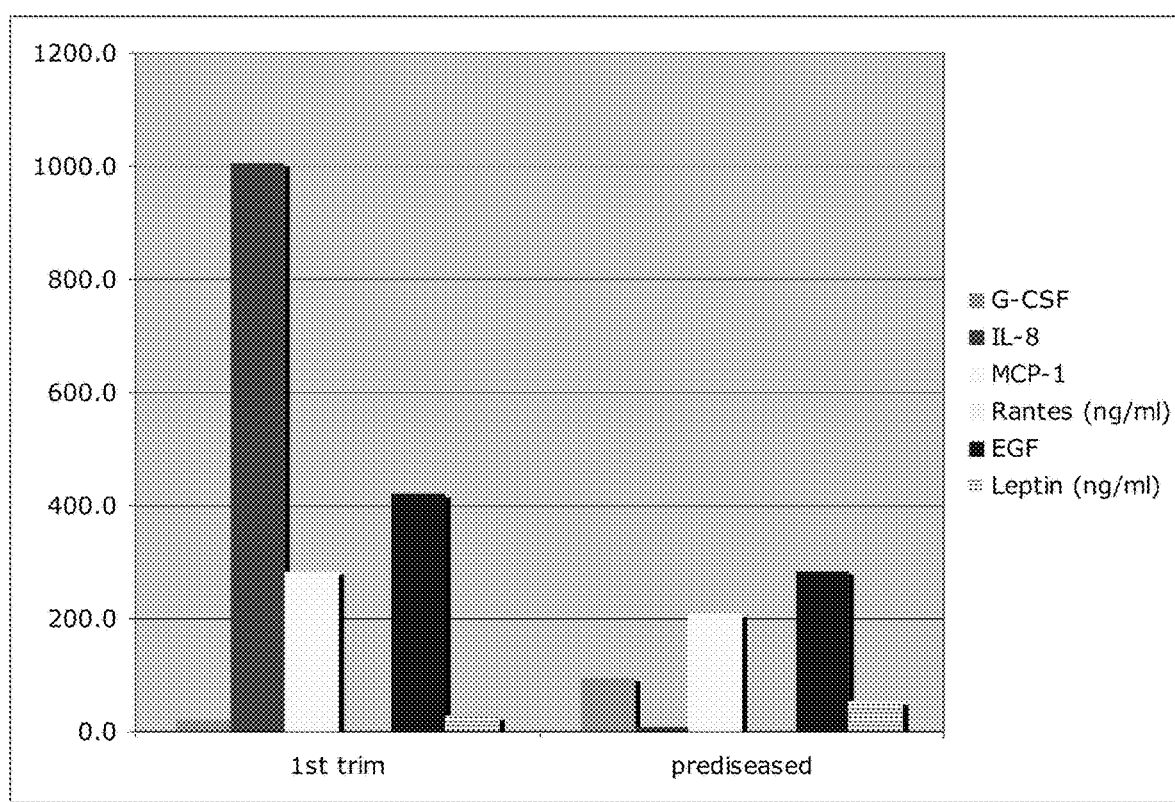
FIG. 14 is a bar graph depicting the serum levels as assessed by Luminex® assays of the indicated proteins in the first trimester of normal and prediseased pregnancies.
Figure 15A:
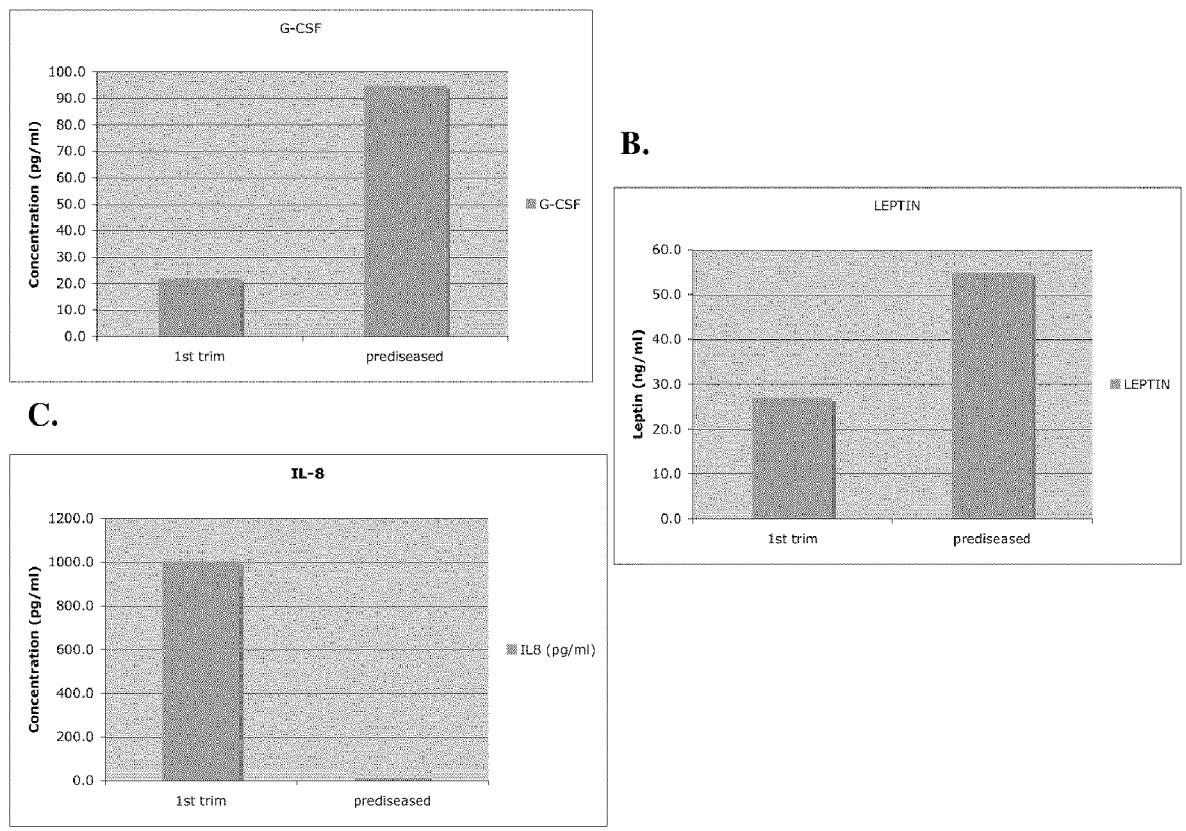

FIG. 5 depicts the results for the indicated biomarkers from Luminex® assays conducted on sera from non-pregnant women and normal pregnant women in their first trimester of pregnancy. FIG. 6 depicts the results for the indicated biomarkers from Luminex® assays conducted on sera from normal pregnant women in their first, second, or third trimester of pregnancy. FIGS. 7-13 depict the results for the biomarkers G-CSF, IL-8, MCP-1, VEGF, EGF, leptin, and secreted FasL, respectively, from Luminex® assays conducted on sera from normal and prediseased pregnant women in their first, second, or third trimester of pregnancy. FIGS. 14 and 15 depict the results for the indicated biomarkers from Luminex® assays conducted on sera from normal and prediseased pregnant women in their first trimester of pregnancy.

Example 2

Effect of Normal and Preeclamptic Serum on Trophoblast Cell Viability Methods

Cells

First trimester H8 trophoblast cell line was maintained in RPMI supplemented with 10% Fetal Bovine Serum (FBS) (Gemini Bioproducts), 1000 units/ml penicillin, 100 µg/ml streptomycin, 10 mM HEPES, 100 nM non-essential amino acids and 1 mM sodium pyruvate (Gibco, Carlsbad, Calif.), at 37° C./5% $CO_2$.

Blood Samples

Blood samples were obtained from normal patients in the first (18), second (19), and third trimester (11), and 12 preeclamptic patients. Pregnancies were considered normal when medical and obstetrical complications of pregnancy were ruled out and birthweight was appropriate-for-gestational-age at term ($\geq$37 gestational weeks). Preeclampsia was defined as hypertension (systolic blood pressure $\geq$140 mmHg or diastolic blood pressure $\geq$90 mmHg on at least two occasions, 4 hours to 1 week apart) and proteinuria (>300 milligrams in a 24 hour urine collection or one dipstick measurement >2+)(21). The medical records of all of the normal control patients were reviewed to confirm that no one had antepartum, intrapartum or postpartum complications. Patients with chronic hypertension, diabetes mellitus, antiphospholipid antibody syndrome, thrombophilic mutations or transient blood pressure elevations were excluded from this study. Approval for this study was obtained through the Human Investigations Committee at Yale University and NICHD.

Cytotoxic Assay

For the cytotoxic assay, 5,000 H8-trophoblast cells/well were plated in a 96 well plate in complete media. Afterwards, cells were incubated in Optimem, (without serum) for 24 hours, thereafter treated with serum from the patients at 10% final concentration in Optimem for 48 hours at 37° C.

Cell viability was assessed with the Cell Titer 96 Aqueous One Solution Cell Proliferation Assay (Promega). This assay is a calorimetric method for determining the number of viable cells in culture. It utilizes 3-(4,5-dimethylthiazol-2-yl)-5-(3-carboxymethoxyphenyl)-2-(4-sulfophenyl)-2H-tetrazolium (MTS) that is bioreduced by cells into a colored formazan product. NADPH accomplishes this conversion or NADH produced by dehydrogenase enzymes in metabolically active cells (53). Thus, the quantity of formazan product, as measured by the amount of absorbance at 490 nm, is directly proportional to the number of living cells in culture. The data is presented as percent viability, which is calculated by subtracting the amount of viable cells in the experimental condition (e.g., trophoblast cells cultured in the presence of serum from a pregnant woman), from the amount of viable cells in the baseline condition (e.g., an equivalent sample of trophoblast cells cultured in the absence of serum from a pregnant woman), divided by the amount of viable cells in the baseline condition, multiplied by 100% (23).

Sensitivity to Fas-mediated Apoptosis

In addition to the serum from normal pregnant controls or from preeclamptic cases, the first trimester H 8 trophoblast cells were treated with an agonist anti Fas antibody or a blocking anti FasL antibody. Anti Fas antibody mimics FasL and promotes apoptosis, while anti-FasL antibody blocks the receptor and inhibits apoptosis. Cell viability was assessed with the Cell Titer 96 Aqueous One Solution Cell Proliferation Assay (Promega). Cell viability was expressed as percentage of the control as described above.

Statistical Analysis

The data were tested for statistical significance by the ANOVA; Bonferroni comparison of means and student t test where appropriate. A p value of <0.05 was considered significant.

Results

Effect of Normal Serum from Each Trimester on Trophoblast Cell Viability

To characterize the effect of normal serum obtained from first, second and third trimesters of pregnancy on trophoblast cell viability, Applicants developed a cytotoxicity assay comprising first trimester H-8 trophoblast cells incubated for 48 hours with the patients' serum. Serum obtained from the first trimester of normal pregnancy induced a 12% reduction in cell viability compared to base line conditions. A 4% increase in cell viability was observed when the trophoblast were exposed to 2nd trimester sera, and a 3% decline in cell viability was seen when 3rd trimester sera were used.

Effect of Serum from Preeclamptic Patients on Trophoblast Viability

Figure 16:
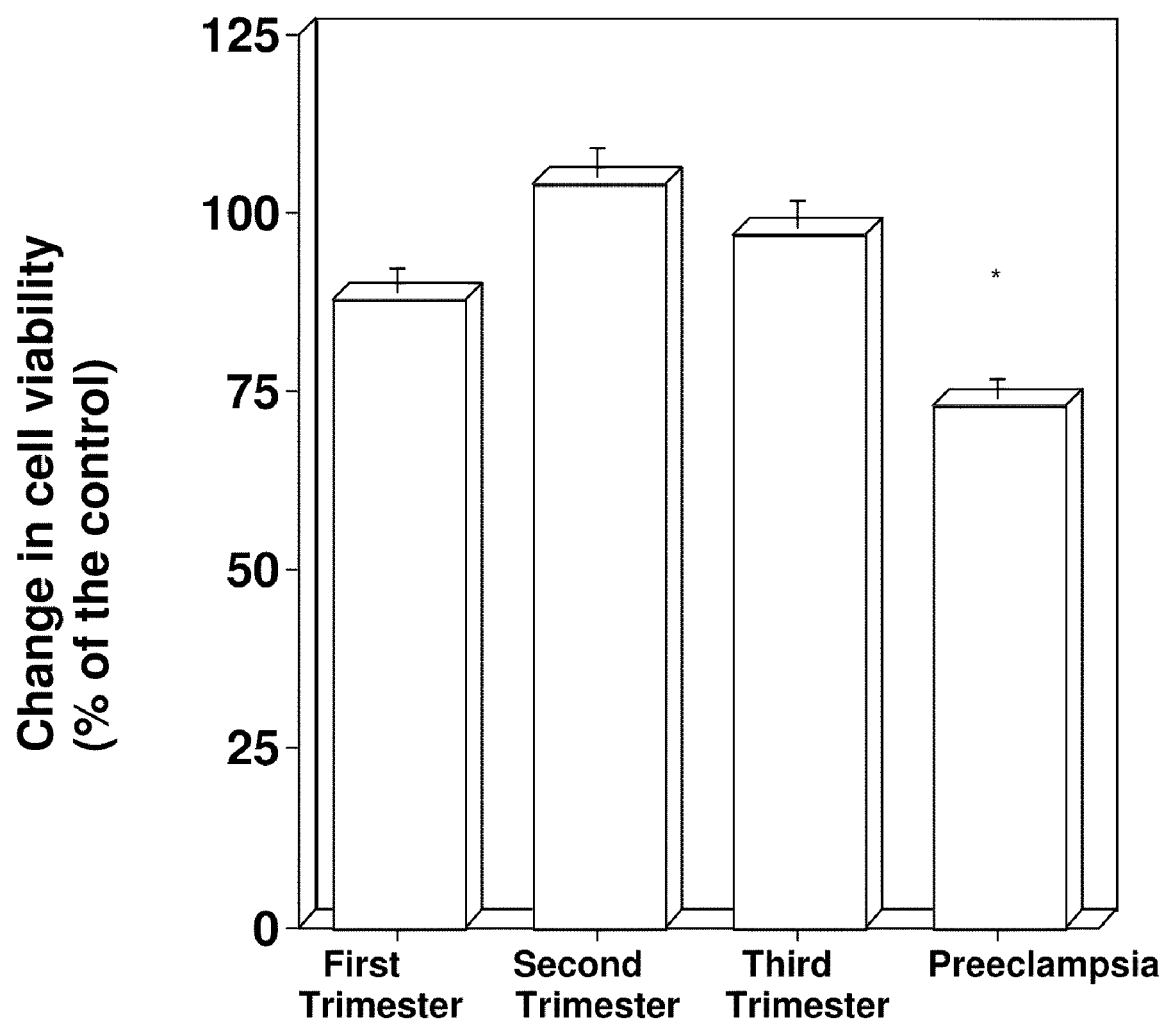
FIG. 16 is a graph depicting the effect of normal and preeclamptic serum on trophoblast cell viability.

Applicants then evaluated the effect of serum obtained from patients with the diagnosis of preeclampsia on trophoblast cell viability. Thus, when the trophoblast cells were exposed to serum from women with preeclampsia, there was a 27% decline in cell viability. This was a significant difference from the normal pregnancy control group (p=0.014; FIG. 16).

Effect of Serum from Preeclamptic Patients on Fas-mediated Apoptosis

Figure 17:
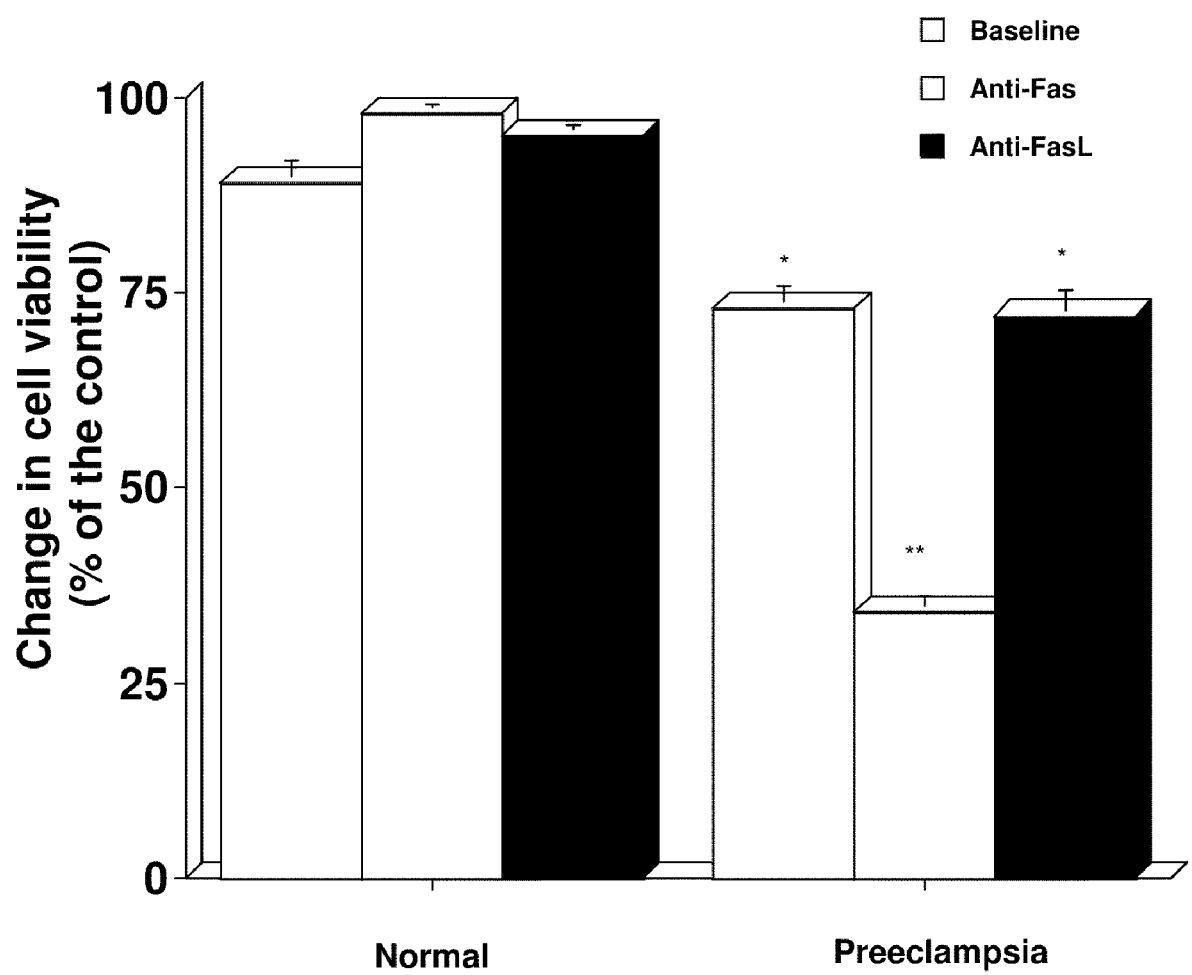
FIG. 17 is a graph depicting the effect of serum from preeclamptic patients on Fas-mediated apoptosis.

In order to elucidate whether the decrease on trophoblast cell viability induced by serum from preeclamptic patients involves Fas-mediated apoptosis, cells were treated during the incubation period with an anti Fas antibody, which mimics FasL and promotes apoptosis, or a blocking anti FasL antibody that blocks the interaction of FasL with Fas and therefore inhibits Fas-mediated apoptosis. In the normal pregnancy control group, the addition of anti Fas or Anti FasL antibodies produced no effect on trophoblast cell viability. In contrast, the addition of anti Fas antibody to the preeclamptic sera further increased cell death to 35% reduction in trophoblast viability compared to the normal (p=0.022). No effect was found following treatment with the anti-FasL antibody. (FIG. 17).

Discussion

Applicants describe a cytotoxic effect of preeclamptic serum on first trimester trophoblast cells. Furthermore, Applicants show that this effect may be related to changes in trophoblast sensitivity to Fas mediated apoptosis.

Apoptosis is an adaptive process to balance cell growth and death, and restore homeostasis. During early pregnancy, the trophoblast is in general resistant to apoptosis allowing the growth and normal invasion of the placenta. Some studies suggest that placental apoptosis may increase as pregnancy progresses. Dysregulation of apoptosis may be related to pathologic conditions such as preeclampsia, intrauterine growth restriction, and possibly pre-term labor (54-56). It has recently been shown that there is increased apoptosis in placental beds of pregnancies complicated by preeclampsia (57).

Applicants have shown a differential effect of serum from normal pregnancies and preeclamptic pregnancies on trophoblast cell viability. While normal serum did not induce significant changes in cell viability, serum from preeclamptic patients had a cytotoxic effect on trophoblast cells. This finding suggests the presence of factor(s) affecting the regulation of apoptosis. Some of these toxic factors may be related to cytokines, which can induce activation of apoptotic genes and promote cell death. Thus, preeclampsia has been related to increase in proinflammatory cytokines such as TNF-α, IL-1, IFNγ, and IL-6 (54, 58, 59). These cytokines have been shown to activate apoptotic genes such as the Fas/FasL system (19) and bcl2 family (57) in trophoblast, leading to aberrant placental invasion, function, and rejection.

It has been demonstrated that anti-inflammatory cytokines increase the resistance of trophoblast cells to Fas-mediated apoptosis, either by inhibiting Fas expression or inducing FLIP activation. On the other hand, pro-inflammatory cytokines increase trophoblast sensitivity to Fas-mediated apoptosis (19). Applicants have found that serum from preeclamptic patients render the trophoblast more sensitive to Fas mediated apoptosis, suggesting the presence of high levels of proinflammatory cytokines.

An important cellular component in preeclampsia is the presence of high levels of activated neutrophils, which constitutes a potential source of pro-inflammatory cytokines, creating a pro-apoptotic milieu at the maternal-fetal interface (60-63).

Applicants suggest that changes in the normal microenvironment at the implantation site influence trophoblast sensitivity to apoptosis, which then may lead to placental damage, impaired trophoblast invasion and pathological conditions such as preeclampsia. The present invention demonstrates a potential link between systemic serum factor(s) and their local effect on trophoblast cell viability. Although the systemic cytotoxic factors have not yet been identified, clearly the differential effect of serum from normal versus preeclamptic patients on trophoblast viability suggests their presence.

Example 3

Applicants investigated whether the sera of women who subsequently develop preeclampsia have a pro-apoptotic effect on trophoblasts.

Study Design

Serum samples were obtained from 96 pregnant women. Fifty-eight samples (28 first trimester, 19 second trimester, 11 third trimester) were obtained from women who remained normotensive throughout the gestation (herein referred to as normal). Thirty-eight samples (14 first trimester, 18 second trimester, 6 third trimester) were from women who were normotensive at the time that the serum samples were obtained and who subsequently developed preeclampsia (herein referred to as pre-disease). Preeclampsia was defined as hypertension (systolic blood pressure ≧140 mmHg or diastolic blood pressure ≧90 mmHg on at least two occasions, 4 hours to 1 week apart) and proteinuria (>300 milligrams in a 24 hour urine collection or one dipstick measurement >2+)(21). The medical records of all of the normal control patients were reviewed to confirm that none of them had antepartum, intrapartum or postpartum complications. Patients with chronic hypertension, diabetes mellitus, antiphospholipid antibody syndrome, thrombophilic mutations or transient blood pressure elevations were excluded. The use of these samples for research purposes was approved by the Human Investigation Committee at Yale University and the NICHD IRB.

Cell Viability Assay

The first trimester human trophoblast cell line, H8, was maintained in RPMI supplemented with 10% FBS (Gemini Bioproducts), 1000 U/ml penicillin, 100 μg/ml streptomycin, 10 mmol/l HEPES, 100 mmol/l non-essential amino acids and 1 mmol/l sodium pyruvate (Gibco, BRL, Gaithersburg, Md., USA), at 37° C./5% $CO_2$. For the assay, trophoblast cells (5000 cells/well) were plated in a 96 well plate in complete media and grown to 80% confluence. Cells were then incubated in OptiMem (Opti-Merr, Gibco BRL) (without serum) for 24 hours, and thereafter treated with serum obtained from the patients at 10% final concentration in OptiMem for 48 hours at 37° C. Cell viability was assessed with the Cell Titer 96 Aqueous One Solution Cell Proliferation Assay (Promega, Madison, Wis., USA). This assay is a colorimetric method for determining the number of viable cells in culture. It utilizes 3-(4,5-dimethylthiazol-2-yl)-5-(3-carboxymethoxphenyl)-2-(4-sulfophenyl)-2H-tetrazolium (MTS) that is bio-reduced by cells into a colored formazan product. All specimens were run in duplicate and repeated at least two times with similar results. The data are presented as percent viability, which is calculated by subtracting the amount of viable cells in the experimental condition (e.g., trophoblast cells cultured in the presence of serum from a pregnant woman), from the amount of viable cells in the baseline condition (e.g., trophoblast cells cultured in the absence of serum from a pregnant woman), divided by the amount of viable cells in the baseline condition, multiplied by 100% (22).

Effect of Normal and Pre-Preeclamptic Serum on Trophoblast Sell Viability

Figure 19:
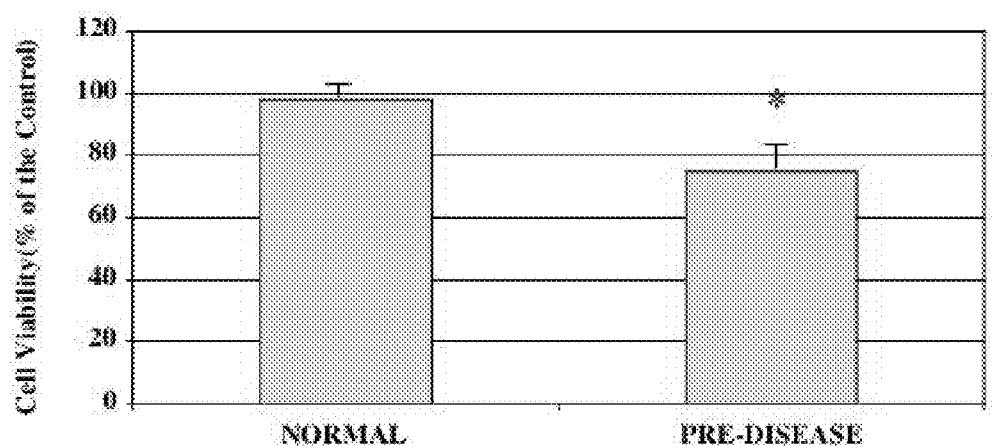
FIG. 19 is a graph depicting the effect of normal and pre-preeclamptic serum on trophoblast cell viability.

The first trimester H8 trophoblast cell line was treated with 10% serum obtained from normotensive women or pre-disease patients in the first, second and third trimesters of pregnancy. Cell viability was determined by the Cell Titer 96 assay. Data are presented as mean+SD percentage of the control (*pre-disease 76%+5% vs. normal pregnancy 97%+4%; p=0.007) (FIG. 19).

Figure 20:
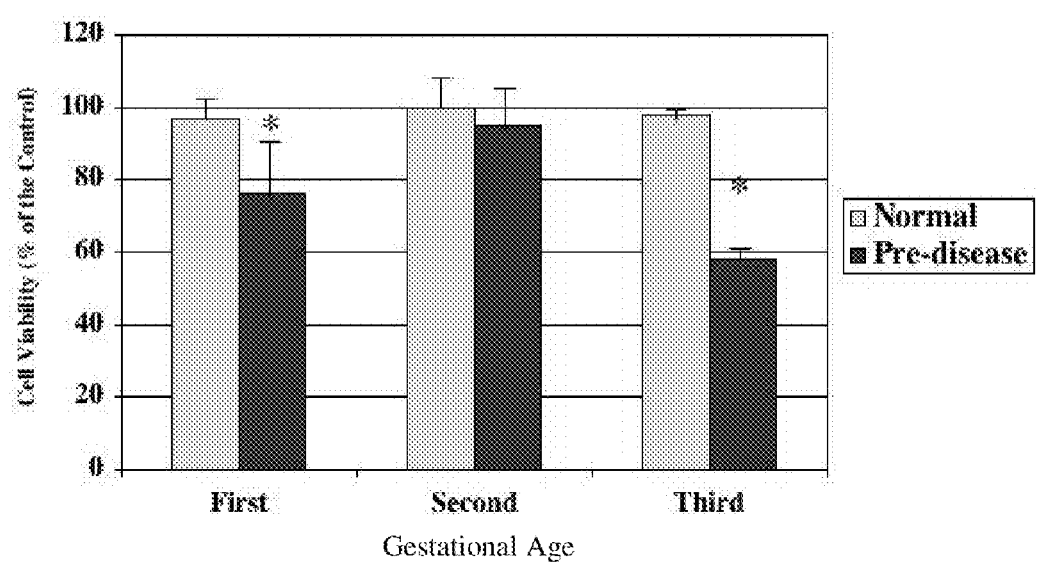
FIG. 20 is a graph depicting the effect of sera from first, second, and third trimester pregnancies on trophoblast cell viability.

Effect of Sera from First, Second and Third Trimester Pregnancies on Trophoblast Cell Viability The first trimester H8 trophoblast cell line was treated with 10% serum obtained from first, second or third trimester of pregnancy of normotensive and pre-disease women. Cell viability was determined by the Cell Titer 96 assay. Data are presented as mean+SD percentage of the control (*p=0.007.p=0.001) (FIG. 20**).

Western Blot Analysis

5×10⁵ cells were plated in 35 mm² petri dishes (BD Biosciences), grown to 70% confluence, and treated with sera as described above. Following treatment, cells were lysed in 1% NP40 and 0.1% SDS in the presence of 0.2 mg/ml PMSF and a protease inhibitor cocktail (Roche Applied Science, Indianapolis, Ind.) on ice for 20 minutes. Cellular debris was removed by centrifugation at 14,000×g at 4° C. Protein concentrations were determined by BCA assay (Pierce Biotechnology, Rockford, Ill.) and 20 μg of each sample was denatured in sample buffer (2.5% SDS, 10% glycerol, 5% b-mercaptoethanol, 0.15 M Tris (pH 6.8) and 0.01% bromophenol blue) and subjected to 12% SDS-PAGE. Proteins were transferred to PVDF membranes (NEN Life Sciences, Boston, Mass.) at 100V for 105 minutes as previously described (23, 24).

Antibodies and concentrations were as follows: rabbit anti-actin (Sigma, 1:10,000), rabbit anti-proform caspase-3 (Santa Cruz, Santa Cruz Calif. 1:1,000), rabbit anti-cleaved caspase-3 (Cell Signaling, 1:1000). Detection of antibody signals was determined by enhanced chemiluminescence detection of peroxidase conjugated secondary antibodies (Vector). The intensity of the signals were analyzed by densitometry and normalized to the Beta-actin signal using a digital imaging analysis system and 1D Image Analysis Software (Kodak Scientific Imaging Systems, Rochester, N.Y.).

Effect of Preeclamptic Sera on Caspase-3 Activation

Figure 21:
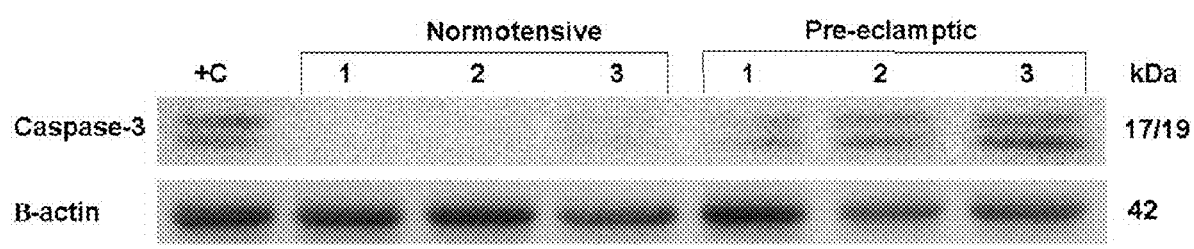
FIG. 21 is a blot depicting the effect of preeclamptic sera on caspase-3 activation.

The first trimester H8 trophoblast cell line was treated with 10% serum obtained from preeclamptic patients for 48 hours. The expression of the active form of caspase-3 was determined by Western blot analysis. Note the presence of the p17 and p19 bands in the trophoblast cells treated with sera from preeclamptic patients, but not in the group treated with sera from normotensive patients (FIG. 21).

Statistical Analysis

The data were tested for statistical significance by the ANOVA, followed by post hoc tests with correction for multiple comparisons and Student t test where appropriate. A p value of <0.05 was considered significant.

Results

Patient Profiles

There were no significance differences in maternal age, gravidity or gestational age at serum collection between the two groups. There were more nulliparous women in the pre-disease group and the mean gestational age at which the diagnosis of preeclampsia was determined was 31.4 weeks (FIG. 18).

Pre-Disease Serum Reduces Trophoblast Cell Viability

In order to determine if sera from pre-disease patients influences trophoblast survival, Applicants initially evaluated the effect of sera from pre-disease vs. normal pregnancies on trophoblast cell viability. Treatment with serum obtained from pre-disease patients induced a statistically significant decrease in H8 trophoblast cell viability compared to the normal, gestational aged matched controls (24% vs. 4% respectively p=0.007; FIG. 19).

Pre-disease Serum from Each Trimester has Differential Effects on Trophoblast Cell Viability Applicants also determined if the effect of pre-disease serum on trophoblast survival was dependent on gestational age. In order to do so, Applicants analyzed the effect of sera obtained from pre-disease and normal patients in the first, second and third trimester of pregnancy. Whereas serum obtained from pre-disease women in the first trimester was associated with a 27% reduction in cell viability (p=0.002; FIG. 20), serum obtained from normal pregnant women in the first trimester showed a 4% reduction in cell viability. Serum obtained from pre-disease women caused an 8% reduction in cell viability (p=0.06; FIG. 20), while serum obtained from normal pregnant women in the second trimester showed a 5% increase in cell viability. Treatment with sera from the pre-disease group in this trimester induced a 41% reduction in cell viability (p=0.001; FIG. 20), whereas serum obtained from normal pregnant women in the third trimester showed a 4% reduction. These results indicate that the decrease in trophoblast cell viability following treatment with pre-disease sera is predominantly detected in the first and third trimester of pregnancy.

Caspase-3 Activation in Trophoblast Cells

In order to determine whether the decrease in trophoblast viability observed in trophoblast cells after treatment with preeclamptic sera was related to the activation of the apoptotic cascade, Applicants evaluated the expression of caspase-3 by Western Blot analysis. As shown in FIG. 21, the active forms of caspase-3 (p19 and p17) were detected in trophoblast cells treated with sera obtained from preeclamptic patients, but not in trophoblast cells treated with sera from normotensive controls. However, all the groups express the pro-form (p30) of caspase-3. This suggests that the apoptotic cascade is activated only in trophoblast cells treated with pre-disease serum.

Caspase-3 Assay

Caspase-3 substrate (Ac-DEVD-pNA) was added to a final concentration of 200 μM in 100 μl reactions containing 100 mM HEPES (pH 7.5), 10% sucrose, 0.1% CHAPS, 2% DMSO, and 10 mM DTT in a 96 well plate. Plates were incubated at 37° C. for 4 hours. Absorbance of the cleaved product was read at 405 nm using Dynatech MR5000 plate reader. Blank values were subtracted and relative activity was calculated based on activity from untreated cells.

REFERENCES

1. ROBERTS J M. Preeclampsia: what we know and what we do not know. Semin Perinatol 2000;24:24-8.
2. Anonymous. Do women with preeclampsia, and their babies, benefit from magnesium sulphate? The Magpie Trial: a randomised placebo-controlled trial. Lancet 2002;359:1877-90.
3. BROSENS I, DIXON H G, ROBERTSON W B. Fetal growth retardation and the arteries of the placental bed. Br J Obstet Gynaecol 1977;84:656-63.
4. PIJNENBORG R. Establishment of uteroplacental circulation. Reprod Nutr Dev 1988;28:1581-1586.
5. KIM Y M, CHAIWORAPONGSA T, GOMEZ R, et al. Failure of physiologic transformation of the spiral arteries in the placental bed in preterm premature rupture of membranes. Am J Obstet Gynecol 2002;187:1137-42.
6. ROBERTSON W B, BROSENS I, DIXON G. Maternal uterine vascular lesions in the hypertensive complications of pregnancy. Perspect Nephrol Hypertens 1976;5:115-27.
7. KHONG T Y, DE WOLF F, ROBERTSON W B, BROSENS I. Inadequate maternal vascular response to placentation in pregnancies complicated by preeclampsia and by small-for-gestational age infants. Br J Obstet Gynaecol 1986; 93:1049-59.
8. ZHOU Y, DAMSKY C H, FISHER S J. Preeclampsia is associated with failure of human cytotrophoblasts to mimic a vascular adhesion phenotype. One cause of defective endovascular invasion in this syndrome? J Clin Invest 1997;99:2152-64.
9. Fisher S J. The placenta dilemma. Semin Reprod Med 2000;18:321-6.
10. De Wolf F, De Wolf-Peeters C, Brosens I. Ultrastructure of the spiral arteries in the human placental bed at the end of normal pregnancy. Am J Obstet Gynecol 1973;117:833-48.
11. De Wolf F, Robertson W B, Brosens I. The ultrastructure of acute atherosis in hypertensive pregnancy. Am J Obstet Gynecol 1975;123:164-74.
12. Buemi M, Allegra A, D'anna R, et al. Is apoptosis cause of preeclampsia? Eur Rev Med Pharmacol Sci 1998;2:185-8.
13. Levy R, Nelson D M. To be, or not to be, that is the question. Apoptosis in human trophoblast. Placenta 2000;21:1-13.
14. Mor G, Straszewski S, Kamsteeg M. Role of the Fas/Fas ligand system in female reproductive organs: survival and apoptosis. Biochem Pharmacol 2002;64:1305.
15. Straszewski S L, Abrahams V M, Funai E, Mor G. Xiap Confers Human Trophoblast Cell Resistance to Fas-Mediated Apoptosis. Molecular Human Reproduction 2004; in press.
16. Smith S C, Baker P N, Symonds E M. Increased placental apoptosis in intrauterine growth restriction. Am J Obstet Gynecol 1997;177:1395-401.
17. Levy R, Smith S D, Yusuf K, et al. Trophoblast apoptosis from pregnancies complicated by fetal growth restriction is associated with enhanced p53 expression. Am J Obstet Gynecol 2002;186:1056-61.
18. Smith S C, Baker P N, Symonds E M. Placental apoptosis in normal human pregnancy. Am J Obstet Gynecol 1997;177:57-65.
19. Aschkenazi S, Straszewski S, Verwer K M, Foellmer H, Rutherford T, Mor G. Differential regulation and function of the fas/fas ligand system in human trophoblast cells. Biol Reprod 2002;66:1853-61.
20. Neale D, Demasio K, Illuzi J, Chaiworapongsa T, Romero R, Mor G. Maternal serum of women with preeclampsia reduces trophoblast cell viability: evidence for an increased sensitivity to Fas-mediated apoptosis. J Matern Fetal Neonatal Med 2003;13:39-44.
21. Gynecologists ACoOa. The Compendium. In: ACOG, ed. Hypertension and pregnancy. Washington D.C., 2000 (vol Technical Bulletin 219).
22. Song J, Rutherford T, Brown S, Mor G. Hormonal regulation of Fas and FasL expression and apoptosis in the normal human endometrium. Molecular Human Reproduction 2002;8:447-455.
23. Song J, Sapi E, Brown W, et al. Roles of Fas and Fas ligand during mammary gland remodeling. J Clin Invest 2000;106:1209-20.
24. Abrahams V, Straszewski S, Kamsteeg M, et al. Epithelial Ovarian Cancer secrete functional Fas Ligand. Cancer Res 2003;63:5573-5581.
25. Williams J. Premature separation of the normally implanted placenta. Surg Gynecol Obstet 1915;21:541-554.
26. Chesley L C. The control of hypertension in pregnancy. Obstet Gynecol Annu 1981;10:69-106.
27. Tatum H J, Mule J G. The hypertensive action of blood from patients with preeclampsia. Am J Obstet Gynecol 1962;83:1028-35.
28. Tatum H J. The Obstetric Patient with Toxemia. Clin Obstet Gynecol 1964;13:233-48.
29. Pirani B B, MacGillivray I. The effect of plasma retransfusion on the blood pressure in the puerperium. Am J Obstet Gynecol 1975;121:221-6.
30. Gant N F, Chand S, Whalley P J, MacDonald P C. The nature of pressor responsiveness to angiotensin II in human pregnancy. Obstet Gynecol 1974;43:854.
31. Gant N F, Daley G L, Chand S, Whalley P J, MacDonald P C. A study of angiotensin II pressor response throughout primigravid pregnancy. J Clin Invest 1973; 52:2682-9.
32. Zuspan F P. Catecholamines. Their role in pregnancy and the development of pregnancy-induced hypertension. J Reprod Med 1979;23:143-50.
33. Zuspan F P. Urinary amine alterations in drug-addiction pregnancy. Am J Obstet Gynecol 1976;126:955-64.
34. Krege J H, Katz V L. A proposed relationship between vasopressinase altered vasopressin and preeclampsia. Med Hypotheses 1990;31:283-7.
35. McKinney E T, Shouri R, Hunt R S, Ahokas R A, Sibai B M. Plasma, urinary, and salivary 8-epi-prostaglandin f2alpha levels in normotensive and preeclamptic pregnancies. Am J Obstet Gynecol 2000;183:874-7.
36. Clark B A, Halvorson L, Sachs B, Epstein F H. Plasma endothelin levels in preeclampsia: elevation and correlation with uric acid levels and renal impairment. Am J Obstet Gynecol 1992;166:962-8.
37. Pedersen E B, Aalkjaer C, Christensen N J, et al. Renin, angiotensin II, aldosterone, catecholamines, prostaglandins and vasopressin. The importance of pressor and depressor factors for hypertension in pregnancy. Scand J Clin Lab Invest Suppl 1984;169:48-56.
38. Aalkjaer C, Johannesen P, Pedersen E B, Rasmussen A, Mulvany M J. Morphology and angiotensin II responsiveness of isolated resistance vessels from patients with preeclampsia. Scand J Clin Lab Invest Suppl 1984;169: 57-60.
39. Chua S, Wilkins T, Sargent I, Redman C. Trophoblast deportation in pre-eclamptic pregnancy. Br J Obstet Gynaecol 1991;98:973-9.
40. Johansen M, Redman C W, Wilkins T, Sargent I L. Trophoblast deportation in human pregnancy—its relevance for preeclampsia. Placenta 1999;20:531-9.
41. Sargent I L, Johansen M, Chua S, Redman C W. Clinical experience: isolating trophoblasts from maternal blood. Ann N Y Acad Sci 1994;731:154-61.
42. Knight M, Redman C W, Linton E A, Sargent I L. Shedding of syncytiotrophoblast microvilli into the maternal circulation in pre-eclamptic pregnancies. Br J Obstet Gynaecol 1998;105:632-40.
43. Kertesz Z, Hurst G, Ward M, et al. Purification and characterization of a complex from placental syncytiotrophoblast microvillous membranes which inhibits the proliferation of human umbilical vein endothelial cells. Placenta 1999;20:71-9.
44. Yoon B H, Romero R, Jun J K, et al. Amniotic fluid cytokines (interleukin-6, tumor necrosis factor-alpha, interleukin-1 beta, and interleukin-8) and the risk for the development of bronchopulmonary dysplasia. Am J Obstet Gynecol 1997;177:825-30.
45. Genbacev O, DiFederico E, McMaster M, Fisher S J. Invasive cytotrophoblast apoptosis in preeclampsia. Hum Reprod 1999;14 Suppl 2:59-66.
46. Miller M J, Voelker C A, Olister S, et al. Fetal growth retardation in rats may result from apoptosis: role of peroxynitrite. Free Radic Biol Med 1996;21:619-29.

47. LOKE Y W, BUTTERWORTH B H, MARGETTS J J, BURLAND K. Identification of cytotrophoblast colonies in cultures of human placental cells using monoclonal antibodies. Placenta 1986;7:221-31.
48. ROBERTS J M, REDMAN C W. Preeclampsia: more than pregnancy-induced hypertension. Lancet 1993;341:1447-51.
49. ASHKENAZI A, DIXIT V M. Death receptors: signaling and modulation. Science 1998;281:1305-8.
50. NAGATA S. Fas and Fas ligand: a death factor and its receptor. Adv. Immunol 1994;57:129-135.
51. NAGATA IS. Apoptosis by death factor. Cell 1997;88: 355-365.
52. MOR G, GUTIERREZ L, ELIZA M, KAHYAOGLU F, ARICI A. Fas-Fas ligand system induced apoptosis in human placenta and gestational trophoblastic disease. American Journal of Reproductive Immunology 1998;40:89-95.
53. BERRIDGE M V, TAN A S. Characterization of the cellular reduction of 3-(4,5-dimethylthiazol-2-yl)-2,5-diphenyltetrazolium bromide (MTT): subcellular localization, substrate dependence, and involvement of mitochondrial electron transport in MTT reduction. Arch Biochem Biophys 1993;303:474-82.
54. ATHAYDE N, ROMERO R, MAYMON E, et al. Interleukin 16 in pregnancy, parturition, rupture of fetal membranes, and microbial invasion of the amniotic cavity. Am J Obstet Gynecol 2000;182:135-41.
55. ROMERO R, MAYMON E, PACORA P, et al. Further observations on the fetal inflammatory response syndrome: a potential homeostatic role for the soluble receptors of tumor necrosis factor alpha. Am J Obstet Gynecol 2000; 183:1070-7.
56. RUDIN C M, THOMPSON C B. Apoptosis and disease: regulation and clinical relevance of programmed cell death. Annu Rev Med 1997;48:267-81.
57. DIFEDERICO E, GENBACEV O, FISHER S J. Preeclampsia is associated with widespread apoptosis of placental cytotrophoblasts within the uterine wall. Am J Pathol 1999;155:293-301.
58. JARVIS J N, DENG L, BERRY S M, ROMERO R, MOORE H. Fetal cytokine expression in utero detected by reverse transcriptase polymerase chain reaction. Pediatr Res 1995;37:450-4.
59. RINEHART B K, TERRONE D A, LAGOO-DEENADAYALAN S, et al. Expression of the placental cytokines tumor necrosis factor alpha, interleukin 1beta, and interleukin 10 is increased in preeclampsia. Am J Obstet Gynecol 1999; 181:915-20.
60. CLARK P, BOSWELL F, GREER I A. The neutrophil and preeclampsia. Semin Reprod Endocrinol 1998;16:57-64.
61. GREER I A, DAWES J, JOHNSTON T A, CALDER A A. Neutrophil activation is confined to the maternal circulation in pregnancy-induced hypertension. Obstet Gynecol 1991; 78:28-32.
62. GREER I A, HADDAD N G, DAWES J, JOHNSTONE F D, CALDER A A. Neutrophil activation in pregnancy-induced hypertension. Br J Obstet Gynaecol 1989;96:978-82.
63. GERVASI M T, CHAIWORAPONGSA T, NACCASHA N, et al. Phenotypic and metabolic characteristics of maternal monocytes and granulocytes in preterm labor with intact membranes. Am J Obstet Gynecol 2001;185:1124-9.

Incorporation by Reference

All publications and patents mentioned herein are hereby incorporated by reference in their entirety as if each individual publication or patent was specifically and individually indicated to be incorporated by reference. In case of conflict, the present application, including any definitions herein, will control.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for determining that a pregnant woman is at risk of developing preeclampsia, comprising comparing the expression of one or more biomarkers in a blood sample from the pregnant woman to be assessed for risk of developing preeclampsia to a predetermined standard for each of the one or more biomarkers, wherein one of the biomarkers is RANTES, and wherein a significant increase in expression of RANTES in the sample as compared to a predetermined standard for RANTES indicates that the pregnant woman is at risk of developing preeclampsia, thereby determining that the pregnant woman is at risk of developing preeclampsia.

2. The method of claim 1, wherein there is more than one biomarker, said biomarker in addition to RANTES selected from the group consisting of: IFNg, I-309, GM-CSF, GDNF, GCP-2, Fraktalkine, Flt-3 Ligand, FGF-7, FGF-6, Eotaxin-3, Eotaxin-2, Eotaxin, EGF, CNTF, CK b 8-1, BMP-6, BMP-4, BLC, BDNF, ANG, MCP-1, LIGHT, Leptin, IL-7, IL-6, IL-5, IL-4, IL-3, IL-2, IL-1ra, IL-1b, IL-1a, IL-16, IL-15, IL-13, IL-10, IGF-1, IGFBP-4, IGFBP-2, IGFBP-1, TNFB, TNFA, TGF-B3, TGF-B1, TARC, SDF-1, SCF, PDGF-BB, PARC, NT-3, NAP-2, MIP-3A, MIP-1D, MIG, MDC, M-CSF, MCP-4, MCP-3, MCP-2, Lymphotactin, I-TAC, IL-8, IL-6R, IL-1 Ra, IL-17, IL-12 P70, IL-12 P40, IL-11, IL-1R1, IL-1 R4/ST2, IGF-1 SR, IGFBP-6, IGFBP-3, ICAM-3, ICAM-1, HGF, HCC-4, GRO-A, GRO, VEGF-D, VEGF, uPAR, TRAIL R4, TRAIL R3, Thrombopoietin, TIMP-2, TIMP-1, TECK, sTNF RI, sTNF RII, SGP130, PlGF, Oncostatin M, Steoprotegin, NT-4, MSP-A, MIP-3B, MIP-1B, MIP-1A, MIF, Fas, and FasL.

3. The method of claim 2, wherein there is more than one biomarker, said biomarker in addition to RANTES selected from the group consisting of: Ang, Leptin, PDGF, ICAM 1, VEGF, G-CSF, Fas, EGF, IGFBP 1, MCP 1, IL8, and FasL.

4. The method of claim 1, wherein the predetermined standard corresponds to the expression levels of the one or more biomarkers in a pregnant woman who is not at risk of developing preeclampsia.

5. The method of claim 4, in which the pregnant woman to be assessed for risk of developing preeclampsia is in the first trimester of pregnancy, wherein the predetermined standard corresponds to the expression levels of the one or more biomarkers in the first trimester of pregnancy.

6. The method of claim 4, in which the pregnant woman to be assessed for risk of developing preeclampsia is in the second trimester of pregnancy, wherein the predetermined standard corresponds to the expression levels of said one or more biomarkers in the second trimester of pregnancy.

7. The method of claim 4, in which the pregnant woman to be assessed for risk of developing preeclampsia is in the third trimester of pregnancy, wherein the predetermined standard corresponds to the expression levels of said one or more biomarkers in the third trimester of pregnancy.

8. The method of claim 1, wherein the method comprises comparing the expression of two or more biomarkers and the determination of risk of developing preeclampsia is based on a score-based classification method.

9. The method of claim 1, wherein the method comprises comparing the expression of two or more biomarkers, wherein the determination of risk of developing preeclampsia is made by comparing a profile of the expression of the two or more biomarkers to a predetermined standard profile for the biomarkers, and wherein a difference in the profiles determines that a pregnant woman is at risk of developing preeclampsia.

10. The method of claim 9, wherein the predetermined standard profile corresponds to the expression profile of the two or more biomarkers in a pregnant woman who is not at risk of developing preeclampsia.

11. The method of claim 10, in which the pregnant woman to be assessed for risk of developing preeclampsia is in the first trimester of pregnancy, wherein the predetermined standard profile corresponds to the expression profile of said two or more biomarkers in the first trimester of pregnancy.

12. The method of claim 10, in which the pregnant woman to be assessed for risk of developing preeclampsia is in the second trimester of pregnancy, wherein the predetermined standard profile corresponds to the expression profile of said two or more biomarkers in the second trimester of pregnancy.

13. The method of claim 10, in which the pregnant woman to be assessed for risk of developing preeclampsia is in the third trimester of pregnancy, wherein the predetermined standard profile corresponds to the expression profile of said two or more biomarkers in the third trimester of pregnancy.

14. The method of claim 9, wherein the predetermined standard profile is determined by comparing the expression of the two or more biomarkers in a pregnant woman to be assessed for risk of developing preeclampsia to the expression of the two or more biomarkers in a pregnant woman who is not at risk of developing preeclampsia using a machine learning technique.

15. The method of claim 1, wherein the predetermined standard is determined by comparing the expression of the one or more biomarkers in the pregnant woman to be assessed for risk of developing preeclampsia to the expression of the one or more biomarkers in a pregnant woman that who is not at risk of developing preeclampsia using support vector machines, K-nearest neighbor classifier, or classification tree analysis.

16. The method of claim 1, wherein there is more than one biomarker, and the biomarker in addition to RANTES is selected from the group consisting of: Ang, Leptin, PDGF, ICAM 1, VEGF, G-CSF, and Fas and an increase in the expression of one or more of the additional biomarkers as compared to the predetermined standard indicates that the pregnant woman is at risk of developing preeclampsia.

17. The method of claim 1, wherein there is more than one biomarker, said biomarker in addition to RANTES selected from the group consisting of: EGF, IGFBP 1, MCP 1, IL8, and FasL and a decrease in the expression of one or more of the additional biomarkers as compared to the predetermined standard indicates that the pregnant woman is at risk of developing preeclampsia.

18. The method of claim 1, wherein the expression of the one or more biomarkers is detected using a reagent that detects the one or more biomarkers.

19. The method of claim 18, wherein the reagent is an antibody or fragment thereof that binds the biomarker.

20. The method of claim 19, wherein the reagent is directly or indirectly labeled with a detectable substance.

21. The method of claim 18, wherein the expression of the one or more biomarkers is detected using mass spectroscopy.

22. The method of claim 1, wherein the expression of the one or more biomarkers is detected by: (a) detecting the expression of a polypeptide which is regulated by the one or more biomarker; (b) detecting the expression of a polypeptide which regulates the biomarker; or (c) detecting the expression of a metabolite of the biomarker.

* * * * *